United States Patent [19]

Melbye et al.

[11] Patent Number: 5,681,302

[45] Date of Patent: Oct. 28, 1997

[54] ELASTIC SHEET-LIKE COMPOSITE

[75] Inventors: William L. Melbye, Woodbury; Dennis L. Becker, Vadnais Heights; Michael R. Gorman, Lake Elmo, all of Minn.

[73] Assignee: Minnesota Mining and Manufacturing Company, St. Paul, Minn.

[21] Appl. No.: 259,485

[22] Filed: Jun. 14, 1994

[51] Int. Cl.⁶ .............................. A61F 13/15; A61F 13/20
[52] U.S. Cl. .............................. 604/373; 604/385.2
[58] Field of Search .............................. 604/358, 365–366, 604/370, 372, 373, 385.1, 385.2; 428/109, 110, 284, 286, 293–294, 296

[56] References Cited

U.S. PATENT DOCUMENTS

| | | | |
|---|---|---|---|
| 3,856,012 | 12/1974 | MacDonald et al. | 604/366 |
| 4,543,099 | 9/1985 | Bunnell et al. | |
| 4,552,795 | 11/1985 | Hansen et al. | |
| 4,618,384 | 10/1986 | Sabee. | |
| 4,640,859 | 2/1987 | Hansen et al. | |
| 4,661,389 | 4/1987 | Mudge et al. | 428/110 |
| 4,781,966 | 11/1988 | Taylor | 604/370 |
| 4,891,258 | 1/1990 | Fahrenkrug | 604/358 |
| 4,894,060 | 1/1990 | Nestegard. | |
| 4,910,064 | 3/1990 | Sabee. | |
| 5,200,246 | 4/1993 | Sabee. | |
| 5,219,633 | 6/1993 | Sabee. | |
| 5,256,231 | 10/1993 | Gorman et al. | |
| 5,354,591 | 10/1994 | Ott et al. | 428/99 |
| 5,451,219 | 9/1995 | Suzuki et al. | 604/358 |

FOREIGN PATENT DOCUMENTS

| | | |
|---|---|---|
| 0 182 942 | 6/1986 | European Pat. Off. . |
| 0 548 609 A1 | 6/1993 | European Pat. Off. . |
| 0 556 749 A1 | 8/1993 | European Pat. Off. . |
| 30 16 197 A1 | 4/1980 | Germany . |
| 3423644 A1 | 6/1984 | Germany . |
| WO 80/00676 | 4/1980 | WIPO . |

OTHER PUBLICATIONS

Brochure "The Microcreping Process for Textiles that imparts: Texture, Shrinkage Control, Soft Hand, Stretch, Bulk . . . " by Micrex Corporation 17 Industrial Road, Walpole, MA 02081 U.S.A. Nov. 1991.

*Primary Examiner*—P. Zuttarelli
*Attorney, Agent, or Firm*—Gary L. Griswold; Walter N. Kim; William L. Huebsch

[57] ABSTRACT

An elastic sheet-like composite comprising a multiplicity of elongate strands of resiliently elastic material, and one or more sheets of material bonded along its length or at sheet bonding locations to the elastic strands, some of which sheets have arcuate portions projecting from the elastic strands between those sheet bonding locations. The elastic sheet-like composite may be incorporated in disposable garments such as diapers or training pants. Also disclosed is a novel method and novel equipment for making the elastic sheet-like composite including in different combinations, sheet corrugating members, equipment for compacting the sheet along its length and an extruder that extrudes the strands onto the sheets and affords versatility in selecting characteristics of the elastic sheet-like composite to be produced without major modifications of the equipment.

30 Claims, 7 Drawing Sheets

ELASTIC SHEET-LIKE COMPOSITE

TECHNICAL FIELD

The present invention relates to elastic sheet-like composites of the type comprising a multiplicity of elongate strands of resiliently elastic material, and one or more sheets of flexible material bonded to the elastic strands; and in certain important aspects, relates to methods and equipment for making such elastic sheet-like composites and products such as disposable garments (including diapers, training pants, and adult incompetence briefs) in which they are used.

BACKGROUND ART

Known are elastic sheet-like composites of the type comprising a multiplicity of elongate strands of resiliently elastic material, and one or more sheets of flexible material anchored at spaced bonding locations to longitudinally spaced parts of the elastic strands so that arcuate portions of the sheets project from the elastic strands between those sheet bonding locations. U.S. Pat. Nos. 4,552,795 and 4,640,859 provide illustrative examples. While the structures of the elastic sheet-like composites described in those patents and the methods and equipment by which they are made are suitable for many purposes, those structures and methods have features that present limitations for certain other purposes.

DISCLOSURE OF INVENTION

The present invention provides improved elastic sheet-like composites generally of the type comprising a multiplicity of elongate strands of resiliently elastic material and one or more sheets of flexible material bonded along sides of the elastic strands; which sheets are extendable with the elongate strands when the elongate strands are stretched either because (1) the sheets have arcuate portions projecting from the elastic strands between portions of the sheets that are bonded to the strands; or (2) the sheets are of stretchable material; or (3) the sheets are of a material that is compacted in the direction in which the strands extend so that the sheet can be extended in that direction; or (4) the sheets have a combination of such structures. These elastic sheet-like composites provides advantages when used for many purposes particularly including being incorporated in disposable garments such as diapers, training pants, or adult incompetence briefs. The present invention also provides novel methods and novel equipment for making the elastic sheet-like composites that causes the elastic sheet-like composites to be well constructed and yet inexpensive to make, and affords versatility in selecting characteristics of the elastic sheet-like composites to be produced without major modifications of the equipment.

According to the present invention there is provided a method for forming an elastic sheet-like composite which comprises (1) providing a first sheet of flexible material (e.g., a polymeric film, or a sheet of woven natural or polymeric fibers, or nonwoven natural or polymeric fibers that are bonded internally of the sheet); (2) forming the first sheet of flexible material to have arcuate portions projecting in the same direction from spaced anchor portions of the first sheet of flexible material; (3) extruding spaced generally parallel elongate strands of molten thermoplastic material that is resiliently elastic when cooled (e.g., elastomeric polyester, polyurethane, polystyrene-polyisoprene-polystyrene, polystyrene-polybutadiene-polystyrene or polystyrene-poly(ethylene-butylene)-polystyrene) onto the anchor portions of the first sheet of flexible material to form, when cooled and solidified, resiliently elastic strands thermally bonded to and extending between the anchor portions of the first sheet of flexible material with the arcuate portions of the first sheet of flexible material projecting from corresponding elongate surface portions of the strands.

By this method there is provided a novel elastic sheet-like composite comprising the multiplicity of generally parallel extruded elongate strands of resiliently elastic thermoplastic material extending in generally parallel spaced relationship, and the first sheet of flexible material that has anchor portions thermally bonded at first sheet bonding locations to longitudinally spaced parts of the elastic strands along corresponding elongate surface portions, and has arcuate portions projecting from those elongate surface portions of the elastic strands between the sheet bonding locations.

Extruding the elastic strands onto the anchor portions of the first sheet of flexible material causes the molten strands to form around and be indented by the arcuate convex surfaces of the anchor portions at the bonding locations with the bonds between the solidified strands and the anchor portions at the bonding locations extending along the entire parts of the strand's surfaces that are closely adjacent the anchor portions. The solidified strands have uniform morphology along their lengths including at those bonding locations and remain elastic at the bonding locations. The strands can be pressed against the convex surfaces of the anchor portions at the bonding locations so that the strands have a greater width between the opposite elongate side surface portions of the strands along the bonding locations than between the bonding locations to provide very firm attachment between the first sheet and the strands. The elastic sheet-like composite can be stretched longitudinally of the elastic strands without breaking that attachment so that the normally arcuate portions of the sheet material or sheet materials can lay along the side surface of the strands. During such stretching, the elastic sheet-like composite according to the present invention provides the advantage that it will retain its width in a direction transverse to the strands instead of necking down or become narrower at its midsection in a direction transverse of the strands (i.e., such narrowing will occur in elastic sheet-like composites which have a resiliently elastic sheet instead of the spaced elastic strands bonded to the anchor portions of the flexible sheet material). The resiliently elastic strands will retain a tension in the elastic sheet-like composite while they are stretched, and when the elastic sheet-like composite is released, will recover to their normal length to again cause those normally arcuate portions of the first sheet material to again be arcuate.

In the method described above for forming an elastic sheet-like composite the forming step can comprise the steps of (1) providing first and second generally cylindrical corrugating members each having an axis and including a multiplicity of spaced ridges defining the periphery of the corrugating member, the ridges having outer surfaces and defining spaces between the ridges adapted to receive portions of the ridges of the other corrugating member in meshing relationship with the sheet of flexible material therebetween; (2) mounting the corrugating members in axially parallel relationship with portions of the ridges in meshing relationship; (3) rotating at least one of the corrugating members; (4) feeding the sheet of flexible material between the meshed portions of the ridges to generally conform the sheet of flexible material to the periphery of the first corrugating member and form the arcuate portions of the sheet of flexible material in the spaces between the ridges of the first corrugating member and the anchor portions of the sheet of flexible material along the outer surfaces of the ridges of the first corrugating member; and (5) retaining the formed sheet of flexible material along the periphery of the first corrugating member for a predetermined distance after movement past the meshing portions of the ridges; and the extruding step includes providing an extruder that, through a die with spaced openings, extrudes the spaced strands of molten thermoplastic material onto the anchor portions of the sheet of flexible material along the periphery of the first corrugating member within the predetermined distance. This method allows the diameter of the strands to be easily varied by either changing the pressure in the extruder by which the strands are extruded (e.g., by changing the extruder screw speed or type) and/or by changing the speed at which the first corrugating member, and thereby the first sheet material, is moved (i.e., for a given rate of output from the extruder, increasing the speed the first sheet material is moved will decrease the diameter of the strands, whereas decreasing the speed at which the first sheet material is moved will increase the diameter of the strands). Also, the die through which the extruder extrudes the elastic thermoplastic material can have an easily changeable die plate in which are formed a row of spaced openings through which the strands of molten thermoplastic material are extruded. Such die plates with openings of different diameters and different spacings can relatively easily be formed by electrical discharge machining to afford different spacings and diameters for the strands. Varied spacing and/or diameters for the openings along the length of the row of openings in one die plate can be used, for example, to produce an elastic sheet-like composite which, when stretched longitudinally of its strands, will be under greater tension adjacent its edges parallel to the strands than at its mid portion between those edges because of larger or more closely spaced strands adjacent its edges. Similar effects can be achieved by shaping and or modifying the die to form hollow strands, strands with shapes other than round (e.g., square or +shaped) or by-component strands.

As indicated above, the elastic sheet-like composite according to the present invention can further include a second sheet of flexible material having anchor portions thermally bonded at second sheet bonding locations to longitudinally spaced parts of the elastic strands along corresponding second elongate surface portions thereof, and having arcuate portions projecting from the second elongate surface portions of the elastic strands between the second sheet bonding locations.

Using the method described above, such a second sheet of flexible material can be provided in the elastic sheet-like composite in at least two different ways. One way is to form the second sheet of flexible material to have arcuate portions projecting in the same direction from spaced anchor portions of the second sheet of flexible material; and positioning the spaced anchor portions of the second sheet of flexible material in closely spaced opposition to the spaced anchor portions of the first sheet of flexible material with the arcuate portions of the first and second sheets of flexible material projecting in opposite directions so that the spaced generally parallel elongate strands of molten thermoplastic material are extruded between and onto the anchor portions of both the first and second sheets of flexible material to form resiliently elastic strands bonded to and extending between the anchor portions of both the first and second sheets of flexible material. Another way is to provide a second sheet of stretchable flexible material that, when stretched, will retain most of the shape to which it is stretched; and to position one surface of the second sheet of flexible material in closely spaced opposition to the spaced anchor portions of the first sheet of flexible material on the side of its spaced anchor portions opposite its arcuate portions so that the spaced generally parallel elongate strands of molten thermoplastic material are extruded between and onto both the anchor portions of the first sheet of flexible material and the adjacent surface of the second sheet of flexible material to form resiliently elastic strands bonded to and extending between the anchor portions of the first sheet of flexible material and extending along and bonded at spaced locations corresponding to those anchor portions along the surface of the second sheet of flexible material; and then to stretch the elastic sheet-like composite longitudinally of the strands after they are cooled and solidified to permanently stretch the second sheet of flexible material so that upon elastic recovery of the elastic strands, the second sheet of flexible material will have arcuate portions projecting from corresponding side surface portions of the strands.

Either or both of the first and second sheets of flexible material in the elastic sheet-like composite can be (1) of polymeric film (e.g., polypropylene, polyethylene or polyester), (2) of conventionally woven flexible fibers or material, (3) of non-woven flexible fibers or material, (4) of multi layer non-woven materials, (5) of nonwoven fibers that are bonded internally of the sheet (e.g., including fibers that are needle punched, hydro entangled, spun bonded, thermally bonded, bonded by various types of chemical bonding such as laytex bonding, powder bonding, etc.) such as fibers of polypropylene, polyethylene, polyester, nylon, cellulose, super absorbent fibers, or polyamide, or combinations of such materials such as a core of polyester and a sheath of polypropylene which provides relatively high strength due to its core material and is easily bonded due to its sheath material, fibers of one material or fibers of different materials or material combinations may be used in the same sheet of material, or (6) fibers or materials of the types described above that have been prepared by the "Microcreping Process for Textiles" using the "Micrex/ Microcreper" equipment available from Micrex Corporation, Walpole, Mass., that bears the U.S. Pat. Nos. 4,894,169; 5,060,349; and 4,090,385, which fibers or materials are crinkled and compressed within the sheet so that the sheet is compacted in a first direction along its surfaces and can be easily expanded in that first direction by partial straightening of the fibers in the sheet. Such sheets of crinkled and compressed fibers can both provide loops for hook and loop fasteners, and can allow the elastic sheet-like composite to be expanded past the condition where the major surfaces of the sheets of crinkled and compressed fibers are straightened, which can be an advantage for some uses of the elastic sheet-like composite. Such first and second sheets should be of polymeric materials that thermally bond with the resiliently elastic thermoplastic material from which the strands are extruded at the temperature of the extrudate, and if such first and second sheets and the resiliently elastic thermoplastic material from which the strands are extruded comprise generally the same thermoplastic material, the extrudate can become fused to the anchor portions of the sheets of polymeric material.

The elastic sheet-like composite can be conveniently included in a disposable garment (e.g., a disposable diaper or training pants or adult incontinence brief) of the type including an outer or covering polymeric layer by adhering the first sheet of flexible material (or the second sheet of flexible material, if present) surface to surface with the outer or covering polymeric layer (e.g., around the waist or leg opening of the garment) so that the strands cause the covering polymeric layer to have arcuate portions projecting away from the first elongate surface portions of the elastic strands between the sheet bonding locations corresponding to the arcuate portions of the first or second sheet of flexible material.

Alternatively, when the disposable garment is a diaper or training pant or adult incontinence brief, the first sheet of flexible material can form the outer or covering layer of the garment with the elastic strands along its inner surface, and conventional absorbent lining or padding material can be positioned along the side of the strands opposite the covering layer. With this structure, the entire covering layer of the disposable garment can be stretched, and the elastic strands may be spaced apart, sized and oriented so that they provide a desired amount of resilient elasticity to keep the garment in place on a person wearing it without applying too much pressure to that person.

The elastic sheet-like composite can also be formed by a method comprising the steps of (1) providing a sheet of stretchable flexible material that when stretched in a first direction will retain most of the length to which it is stretched; (2) extruding spaced generally parallel elongate strands of molten thermoplastic material that is resiliently elastic when cooled; (3) thermally bonding together spaced anchor portions of the first sheet of flexible material and spaced portions of the resiliently elastic strands so that the strands extend in the first direction between the anchor portions of the first sheet of flexible material with a side surface of the first sheet of flexible material laying along elongate side surface portions of the strands; and (4) cooling and solidifying the strands. Such elastic sheet-like composite can be stretched longitudinally of the strands so that upon elastic recovery of the strands, the sheet of flexible material will have arcuate portions projecting from corresponding side surface portions of the strands.

Additionally, the elastic sheet-like composite can also be formed by a method comprising the steps of (1) providing a sheet of flexible material having opposite major surfaces; (2) compacting the sheet in a first direction parallel to the surfaces so that the compacted sheet can be extended in the first direction in the range of 1.1 to over 4 times (and preferably over 1.3 times) its compacted length in the first direction; (3) extruding spaced generally parallel elongate strands of molten thermoplastic material that is resiliently elastic when cooled onto one of the surfaces of the compacted sheet to form resiliently elastic strands thermally bonded to and extending in the first direction along the first compacted sheet; and (4) cooling and solidifying the strands.

BRIEF DESCRIPTION OF DRAWING

The present invention will be further described with reference to the accompanying drawing wherein like reference numerals refer to like parts in the several views, and wherein.

DETAILED DESCRIPTION

Figure 1:
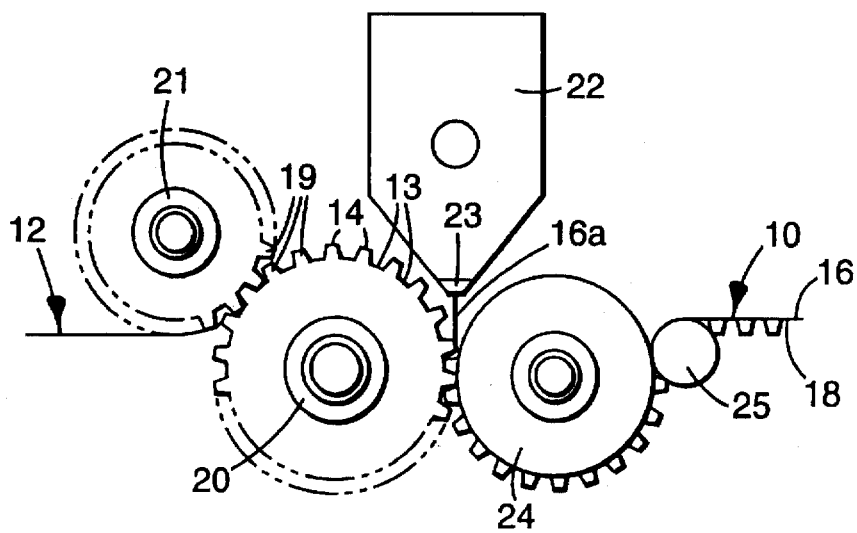
FIG. 1 is a schematic view illustrating a first embodiment of a method and equipment according to the present invention for making a first embodiment of an elastic sheet-like composite according to the present invention.
Figure 2:
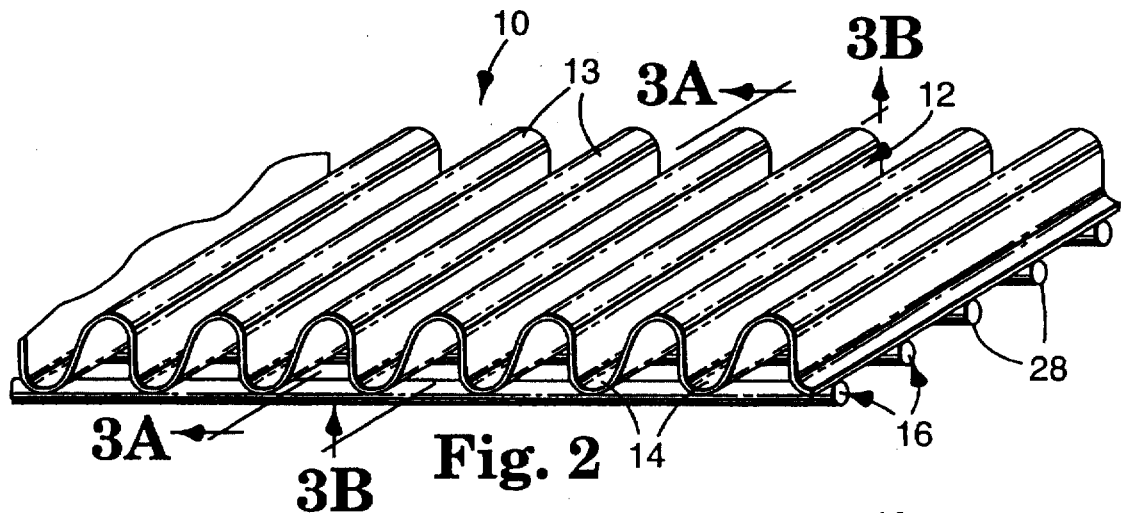
FIG. 2 is a perspective view of the first embodiment of the elastic sheet-like composite according to the present invention made by the method and equipment illustrated in FIG. 1.

Referring now to FIG. 1 of the drawing, there is schematically illustrated a first embodiment of a method and equipment according to the present invention for making a first embodiment of an elastic sheet-like composite 10 according to the present invention which is illustrated in FIGS. 2 and 3.

Generally the method illustrated in FIG. 1 involves providing a first sheet 12 of flexible material; forming the first sheet 12 of flexible material to have arcuate portions 13 projecting in the same direction from spaced anchor portions 14 of the first sheet 12 of flexible material; extruding spaced generally parallel elongate strands 16a of molten thermoplastic material that is resiliently elastic when cooled onto the anchor portions 14 of the first sheet 12 of flexible material to form resiliently elastic strands 16 thermally bonded to and extending between the anchor portions 14 of the first sheet 12 of flexible material with the arcuate portions 13 of the first sheet 12 of flexible material projecting from corresponding elongate side surface portions 18 of the strands 16; and cooling and solidifying the strands 16.

As illustrated in FIG. 1, the equipment for performing the method includes first and second generally cylindrical corrugating members 20 and 21 each having an axis and including a multiplicity of spaced ridges 19 defining the periphery of the corrugating member 20 or 21, the ridges 19 having outer surfaces and defining spaces between the ridges 19 adapted to receive portions of the ridges 19 of the other corrugating member in meshing relationship with the first sheet 12 of flexible material therebetween; means for mounting the corrugating members 20 and 21 in axially parallel relationship with portions of the ridges 19 in meshing relationship; means for rotating at least one of the corrugating members 20 or 21 so that when the first sheet 12 of flexible material is fed between the meshed portions of the ridges 19 the first sheet 12 of flexible material will be generally conformed to the periphery of the first corrugating member 20 to form arcuate portions 13 of the first sheet 12 of flexible material in the spaces between the ridges 19 of the first corrugating member 20 and to form anchor portions 14 of the first sheet 12 of flexible material along the outer surfaces of the ridges 19 of the first corrugating member 20; means (i.e., including the surface of the first corrugating member 20 being roughened by being sand blasted or chemically etched and being heated to a temperature generally in the range of 25 to 150 Fahrenheit degrees above the temperature of the first sheet 12 of flexible material) for retaining the formed first sheet 12 of flexible material along the periphery of the first corrugating member 20 for a predetermined distance after movement past the meshing portions of the ridges 19; means in the form of an extruder feeding a die 22 with a changeable die plate 23 (see FIG. 7) with spaced through openings 40 for extruding resiliently elastic thermoplastic material (e.g., elastomeric polyester, polyurethane, polystyrene-polyisoprene-polystyrene, polystyrene-polybutadiene-polystyrene or polystyrene-poly (ethylene-butylene)-polystyrene, or the elastomeric polyolefin described in European Patent Application No. 0,416815, the content whereof is incorporated herein by reference, or the elastomeric low density polyethylene sold by Dow Chemical under the trade name "Engage" which is made using "Insite" technology) to form a multiplicity of generally parallel elongate molten strands 16a of the resiliently elastic thermoplastic material extending in generally parallel spaced relationship and for positioning the molten strands 16a on the anchor portions 14 of the first sheet 12 of flexible material along the periphery of the first corrugating member 20 within the predetermined distance. Also, that equipment further includes a generally cylindrical cooling roll 24 having an axis; means for rotatably mounting the cooling roll 24 in axially parallel relationship with the corrugating members 20 and 21 with the periphery of the cooling roll 24 closely spaced from and defining a nip with the periphery of the first corrugating member 20 at the predetermined distance from the meshing portions of the ridges 19; and means including a nipping roller 25 for moving the elastic sheet-like composite 10 for a predetermined distance around the periphery of the cooling roll 24 past the nip with the strands 16 in contact with the cooling roll 24 to cool and solidify the strands 16.

Figure 3A:
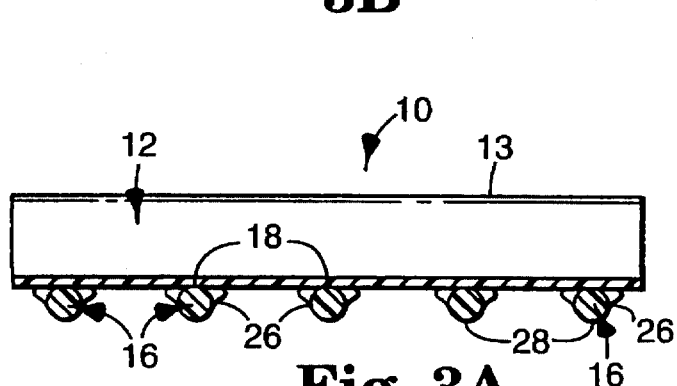
FIG. 3A is a fragmentary enlarged sectional view taken approximately along line 3A—3A of FIG. 2.
Figure 3B:
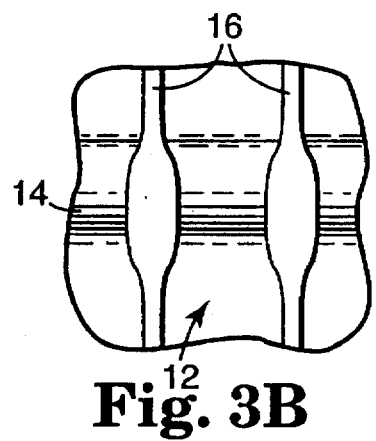
FIG. 3B is a fragmentary enlarged sectional view taken approximately along line 3B—3B of FIG. 2.

The structure of the elastic sheet-like composite 10 made by the method and equipment illustrated in FIG. 1 is best seen in FIGS. 2, 3A and 3B. The elastic sheet-like composite 10 comprises the multiplicity of generally parallel elongate strands 16 of resiliently elastic thermoplastic material extending in generally parallel spaced relationship. Each of the strands 16 is generally cylindrical and has opposite elongate side surface portions 26 (See FIG. 3A) that are spaced from and are adjacent the elongate side surface portions 26 of adjacent strands; and each of the strands 16 also has corresponding opposite first and second elongate surface portions 18 and 28 extending between its opposite elongate side surface portions 26. The spaced anchor portions 14 of the first sheet 12 of flexible material are thermally bonded at first sheet bonding locations to longitudinally spaced parts of the strands 16 along their first elongate surface portions 18, and the arcuate portions 13 of the first sheet 12 of flexible material project from the first elongate surface portions 18 of the elastic strands 16 between the first sheet bonding locations. The first sheet bonding locations are spaced about the same distances from each other and aligned in generally parallel rows extending transverse of the strands 16 to form continuous rows of the arcuate portions 13 projecting about the same distance from the first surface portions 18 of the strands 16. Because the elastic strands 16 have been extruded in molten form onto the anchor portions 14 of the first sheet 12 of flexible material they can be pressed onto the anchor portions 14 of the first sheet 12 by the spacing between the ridges 19 on the first corrugating member 20 and the periphery of the cooling roll 24, in which case the molten strands 16 form around and are indented by the arcuate convex adjacent surfaces of the anchor portions 14. The bonds between the strands 16 and the anchor portions 14 at the first sheet bonding locations extend along the entire parts of the strand's surfaces that are closely adjacent the anchor portions 14. As is illustrated in FIG. 3B, those parts of the strand's surfaces that are closely adjacent the anchor portions 14 can be widened along the surfaces of the anchor portions 14 by the indentations of the strands 16 by the anchor portions 14. Thus the areas of bonding between the strands 16 and the anchor portions 14 are at least as wide and can advantageously be made wider between their opposite elongate side surface portions along their sheet bonding locations than between their sheet bonding locations at the anchor portions 14.

Alternative structures that could be provided for the elastic sheet-like composite 10 include spacing the ridges 19 around the corrugating members 20 and 21 to produce repetitive patterns of different spacings between the anchor portions 14 of the first sheet 12, thereby causing the continuous rows of the arcuate portions 13 to project at different distances from the first surface portions 18 of the strands 16.

Figure 4:
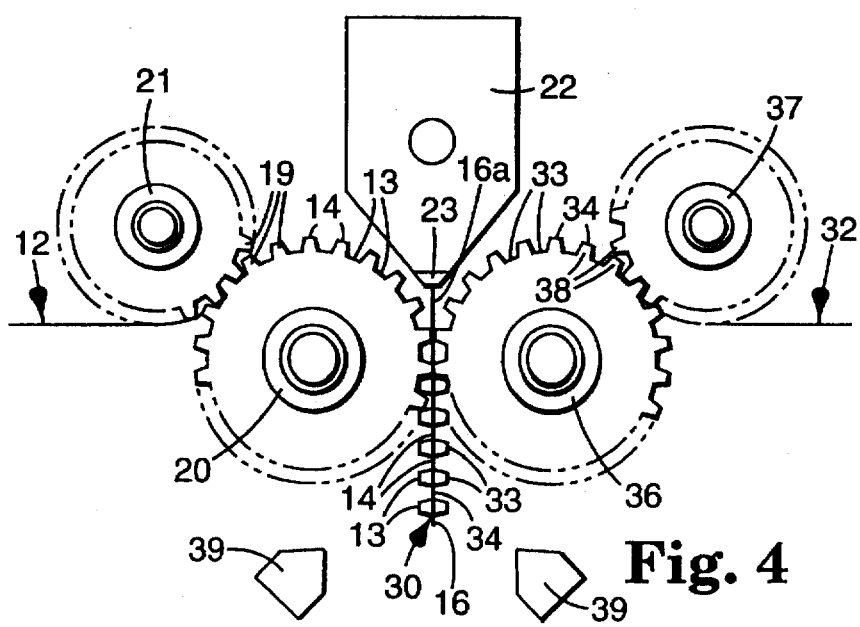
FIG. 4 is a schematic view illustrating a second embodiment of a method and equipment according to the present invention for making a second embodiment of an elastic sheet-like composite according to the present invention.
Figure 5:
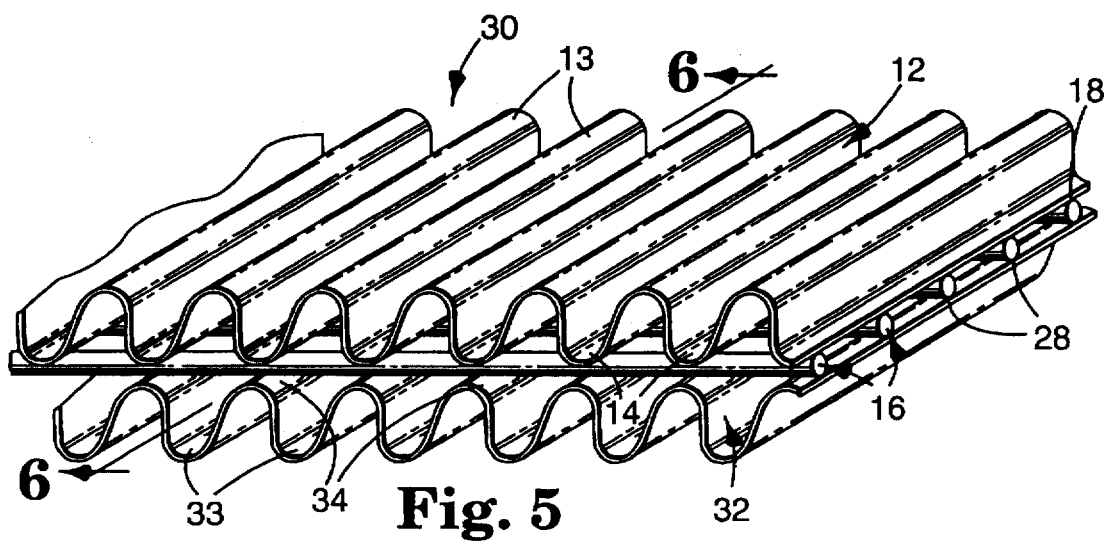
FIG. 5 is a perspective view of the second embodiment of the elastic sheet-like composite according to the present invention made by the method and equipment illustrated in FIG. 4.
Figure 6:
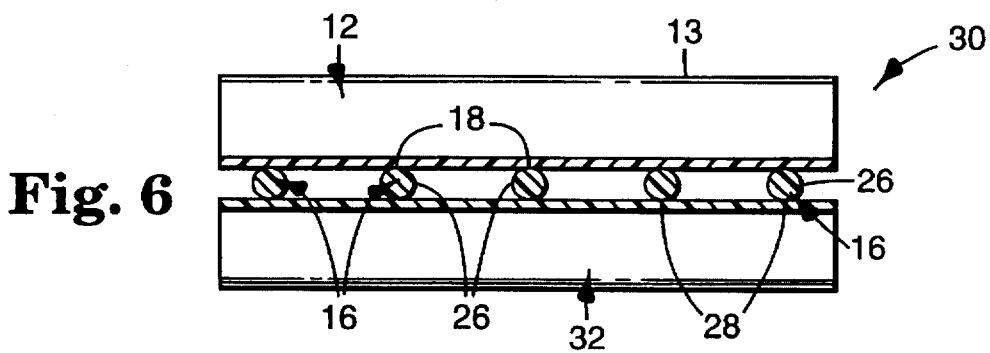
FIG. 6 is a fragmentary enlarged sectional view taken approximately along line 6—6 of FIG. 5.

FIG. 4 illustrates a second embodiment of a method and equipment according to the present invention for making a second embodiment of an elastic sheet-like composite 30 according to the present invention, which sheet 30 is illustrated in FIGS. 5 and 6. The method illustrated in FIG. 4 is somewhat similar and uses much of the same equipment as is illustrated in FIG. 1, and similar portions of that equipment have been given the same reference numerals and perform the same functions as they do in the equipment illustrated in FIG. 1. In addition to the general method steps described above with reference to FIG. 1, the method illustrated in FIG. 4 further generally includes the steps of providing a second sheet 32 of material (e.g., polymeric or other material that could be a sheet or film or could be a nonwoven layer); forming the second sheet 32 of material to have arcuate portions 33 projecting in the same direction from spaced anchor portions 34 of the second sheet 32 of material; and positioning the spaced anchor portions 34 of the second sheet 32 of material in closely spaced opposition to the spaced anchor portions 14 of the first sheet 12 of flexible material with the arcuate portions 13 and 33 of the first and second sheets 12 and 32 of material projecting in opposite directions; and the extruder die 23 extrudes the spaced generally parallel elongate strands 16a of molten thermoplastic material between and onto the anchor portions 14 and 34 of both the first and second sheets 12 and 32 of material to form resiliently elastic strands 16 bonded to and extending between the anchor portions 14 and 34 of both the first and second sheets 12 and 32 of material with the arcuate portions 13 and 33 of the first and second sheets 12 and 32 of material projecting in opposite directions from opposite corresponding first and second elongate side surface portions 18 and 28 of the strands 16.

The equipment illustrated in FIG. 4, in addition to the first and second corrugating members 20 and 21, and the extruder 22 which are operated in the manner described above with reference to FIG. 1, further includes third and fourth generally cylindrical corrugating members 36 and 37 each having an axis and including a multiplicity of spaced ridges 38 defining the periphery of the corrugating member 36 or 37, the ridges 38 having outer surfaces and defining spaces between the ridges 38 adapted to receive portions of the ridges 38 of the other corrugating member 36 or 37 in meshing relationship with the second sheet 32 of flexible material therebetween; means (which could be provided by a frame, not shown) for mounting the third and fourth corrugating members 36 and 37 in axially parallel relationship with portions of the ridges 38 in meshing relationship; means for rotating at least one of the third and fourth corrugating members 36 and 37 so that when the second sheet 32 of material is fed between the meshed portions of the ridges 38 the second sheet 32 of material will be generally conformed to the periphery of the third corrugating member to form arcuate portions 33 of the second sheet 32 of material in the spaces between the ridges 38 of the third corrugating member 36 and to form anchor portions 34 of the second sheet 32 of material along the outer surfaces of the ridges 38 of the third corrugating member 36; and means (i.e., including the surface of the third corrugating member 36 being texturized or roughened by being sand blasted or chemically etched and being heated to a temperature generally in the range of 25 to 150 Fahrenheit degrees above the temperature of the first sheet 32 of flexible material) for retaining the formed second sheet 32 of material along the periphery of the third corrugating member 36 for a predetermined distance after movement past the meshing portions of the ridges 38 of the third and fourth corrugating members 36 and 37. The third corrugating member 36 is positioned in spaced relationship from the first corrugating member 20 so that the extruder die 22 positions the molten strands 16a on the anchor portions 14 and 34 of both the first and second sheets 12 and 32 of material along the peripheries of the first and third corrugating members 20 and 36 within the predetermined distance. Air ducts 39 are provided to blow streams of cool air against opposite sides of the elastic sheet-like composite 30 to solidify the strands 16a and the bond between the strands 16a and the anchor portion 14 and 34 of the sheets 12 and 32.

The structure of the elastic sheet-like composite 30 made by the method and equipment illustrated in FIG. 4 is best seen in FIGS. 5 and 6. The elastic sheet-like composite 30 comprises the multiplicity of generally parallel elongate strands 16 of resiliently elastic thermoplastic material extending in generally parallel spaced relationship. Each of the strands 16 has opposite elongate side surface portions 26 (See FIG. 6) that are spaced from and are adjacent the elongate side surface portions 26 of adjacent strands; and each of the strands 16 also has corresponding opposite first and second elongate surface portions 18 and 28 extending between its opposite elongate side surface portions 26. The spaced anchor portions 14 of the first sheet 12 of flexible material are thermally bonded at first sheet bonding locations to longitudinally spaced parts of the strands 16 along their first elongate surface portions 18, and the arcuate portions 13 of the first sheet 12 of flexible material project from the first elongate surface portions 18 of the elastic strands 16 between the first sheet bonding locations. The second sheet 32 of material has its spaced anchor portions 34 thermally bonded at second spaced sheet bonding locations to longitudinally spaced parts of the strands 16 along their second elongate surface portions 28, and has its arcuate portions 33 projecting from the second elongate surface portions 28 of the elastic strands 16 between the second sheet bonding locations. The first and second sheet bonding locations are opposed to each other, are spaced about the same distances from each other, and are aligned in generally parallel rows extending transverse of the strands 16 to form continuous rows of the arcuate portions 13 and 33 projecting about the same distances from the first and second surface portions 18 and 28 of the strands 16. Because the elastic strands 16 have been extruded in molten form onto the anchor portions 14 and 34 of both the first and second sheets 12 and 32, the molten strands 16 can form around and be indented on opposite sides by the arcuate convex adjacent surfaces of the anchor portions 14 and 34. The bonds between the strands 16 and the anchor portions 14 and 34 at the first and second sheet bonding locations extend along the entire parts of the strand's surfaces that are closely adjacent the anchor portions 14 and 34, which parts can be widened along the surfaces of the anchor portions 14 and 34 by the indentations of the strands 16 by the anchor portions 14 and 34. Thus, the areas of bonding between the strands 16 and the anchor portions 14 and 34 are at least as wide and can be wider between their opposite elongate side surface portions along their sheet bonding locations than between sheet bonding locations at the anchor portions 14 and 34.

Alternative structures that could be provided for the elastic sheet-like composite 30 (in addition to the alternate structures noted above for the sheet like composite 10) include spacing the anchor portions 14 of the first sheet 12 and the anchor portions 34 of the second sheet 32 at different spacings along the strands 16 and/or causing the continuous rows of the arcuate portions 13 and 33 to project at different distances from the first and second surface portions 18 and 28 of the strands 16; or causing one of the sheets 12 or 32 to be discontinuous along its length, or across its width.

Figure 7:
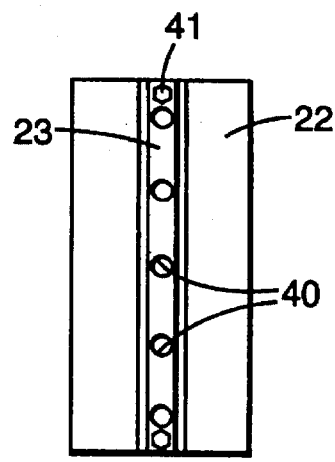
FIG. 7 is a fragmentary front view of a die plate included in the equipment illustrated in FIGS. 1 and 4.

FIG. 7 illustrates the face of the die 22 through which the molten strands 16a of molten thermoplastic material are extruded. The die 22 has spaced openings 40 (e.g., 0.762 millimeter or 0.03 inch diameter openings spaced 2.54 millimeter or 0.1 inch center to center) in its die plate 23 preferably formed by the known electrical discharge machining technique. The die plate 23 is retained in place by the bolts 41, and can be easily replaced with a die plate with openings of different or varied sizes, which openings are spaced on different or varied centers to produce a desired pattern of strands from the die 22.

Figure 8:
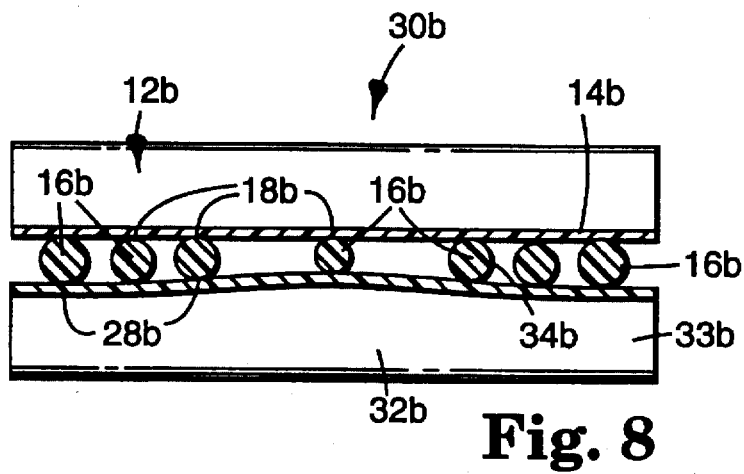
FIG. 8 is a fragmentary sectional view similar to that of FIG. 6 which illustrates possible variations in the size and spacing of strands included in the elastic sheet-like composite.

FIG. 8 illustrates an elastic sheet-like composite 30b similar to that illustrated in FIGS. 5 and 6 and in which similar parts are identified with similar reference numerals except for the addition of the suffix "b". FIG. 8 shows one of many possible variations in the spacing and diameters of the strands 16b that can cause the elastic sheet-like composite 30b when stretched longitudinally of its strands 16b to be under greater or lesser tensions across its width normal to the strands depending on the spacing and or diameters of the strands 16b.

Figure 9:
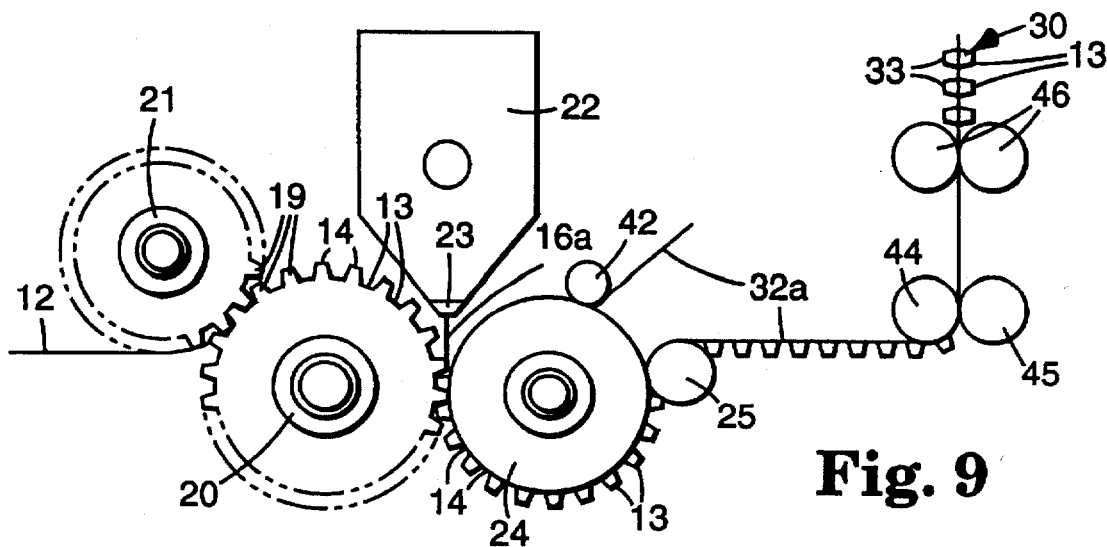
FIG. 9 is a schematic view illustrating a third embodiment of a method and equipment according to the present invention for making the second embodiment of the elastic sheet-like composite according to the present invention illustrated in FIG. 5.

FIG. 9 illustrates a third embodiment of a method and equipment according to the present invention for making the elastic sheet-like composite 30 according to the present invention. The method illustrated in FIG. 9 is quite similar to and uses most of the same equipment as is illustrated in FIG. 1, and similar portions of that equipment have been given the same reference numerals and perform the same functions as they do in the equipment illustrated in FIG. 1. In addition to the general method steps described above with reference to FIG. 1, the method illustrated in FIG. 9 further generally includes the steps of providing a second sheet 32a of stretchable flexible material that when stretched will retain most of the shape to which it is stretched; and positioning one surface of the second sheet 32a of flexible material in closely spaced opposition to the spaced anchor portions 14 of the first sheet 12 of flexible material on the side of the spaced anchor portions 14 opposite the arcuate portions 13 of the first sheet 12 of flexible material so that the extruder die 22 extrudes the spaced generally parallel elongate strands of molten thermoplastic material between and onto both the anchor portions 14 of the first sheet 12 of flexible material and the adjacent surface of the second sheet 32a of flexible material to form resiliently elastic strands 16 bonded to and extending between the anchor portions 14 of the first sheet 12 of flexible material and extending along and bonded to spaced locations along the surface of the second sheet 32a of flexible material opposite the anchor portions 14 of the first sheet 12 of flexible material; and then stretching the elastic sheet-like composite 32a longitudinally of the strands 16 after they are cooled and solidified to permanently stretch the second sheet 32a of flexible material so that upon elastic recovery of the strands 16, the second sheet 32a of flexible material will have arcuate portions 33 projecting from corresponding side surface portions 28 of the strands 16.

The equipment illustrated in FIG. 9, in addition to the first and second corrugating members 20 and 21, the extruder and extruder die 22, the cooling and nipping rollers 24 and 25 which are operated in the manner described above with reference to FIG. 1, further includes a nipping roller 42 that by rotation of the cooling roll 24 allows the second sheet 32a of flexible material to be fed into the nip between the cooling roll 24 and the first corrugating member 20, a pair of nipping rollers 44 and 45 (the roller 44 of which may be heated so that it heats the second sheet 32a after it is attached to the strands 16 in that nip if that is desired or needed to process the composite 30), and a pair of nipping rollers 46 that are rotated at a surface speed sufficiently faster than that of the nipping rollers 44 and 45 to stretch the second sheet 32a in the manner described above, so that after the elastic sheet-like composite 30 moves past the nipping rollers 46 the strands 16 will return to their normal or un-stretched length, and the second sheet 32a of flexible material will have arcuate portions 33 projecting from corresponding side surface portions 28 of the strands 16. The flat, non-corrugated second sheet 32a could, for example, be made of 3M brand porous film (XMO-8-044), which is a stretchable porous polymeric film material that when stretched will retain most of the shape to which it is stretched and for which the roller 44 should be heated to facilitate such stretching; or alternatively could be made of material that has been compacted (e.g., compacted or shortened along its length at up to a 4 to 1 ratio so that its compacted length can be only one quarter or less than the original length) using the Micrex process described above which allows for longitudinal stretching of the second sheet 32a after it is bonded to the strands 16, and normally does not benefit from the roller 44 being heated.

Figure 10:
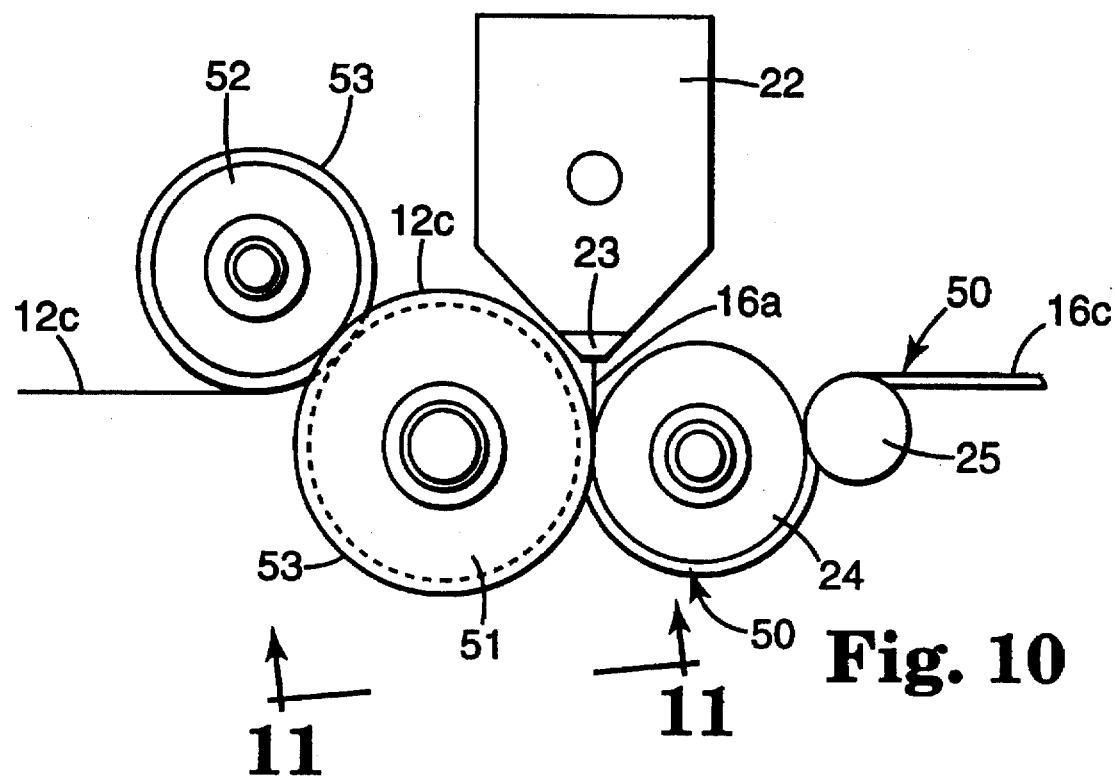
FIG. 10 is a schematic view illustrating a fourth embodiment of a method and equipment according to the present invention for making a third embodiment of the elastic sheet-like composite according to the present invention.
Figure 11:
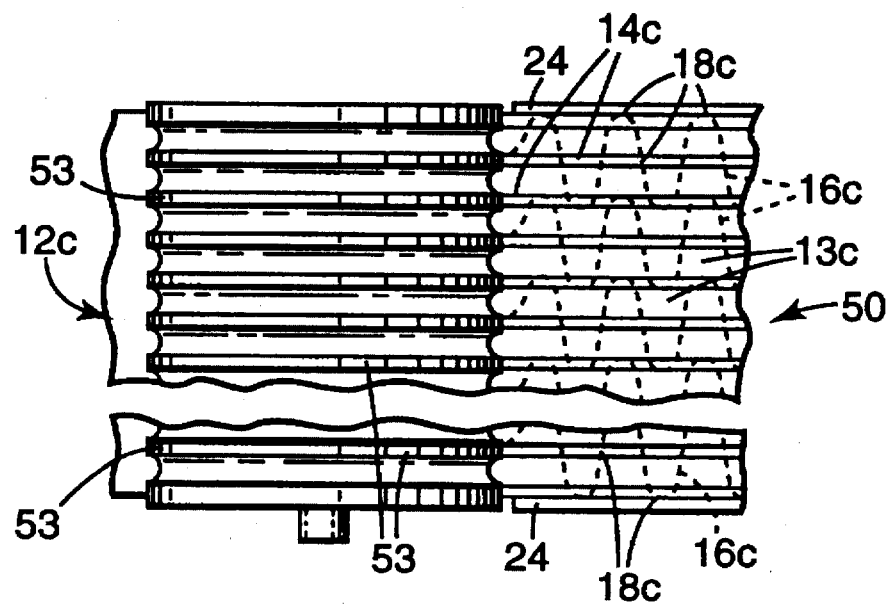
FIG. 11 is a fragmentary view taken approximately along line 11 of FIG. 10.

FIGS. 10 and 11 illustrate a fourth embodiment of a method and equipment according to the present invention for making an elastic sheet-like composite 50 according to the present invention. The elastic sheet-like composite 50 has portions that are similar to corresponding portions of the elastic sheet-like composite 10, and have been given the same reference numerals with the addition of the suffix "c". The method illustrated in FIGS. 10 and 11 uses some of the same equipment as is illustrated in FIG. 1, and similar portions of that equipment have been given the same reference numerals and perform the same functions as they do in the equipment illustrated in FIG. 1. The first and second corrugating members 20 and 21 of FIG. 1, however, have been replaced by first and second cylindrical corrugating members or rollers 51 and 52 each having an axis and including a plurality of generally annular, circumferentially extending, axially spaced parallel elongate ridges 53 around and defining its periphery, with the ridges 53 having outer surfaces and defining spaces between the ridges 53 adapted to receive portions of the ridges 53 of the other corrugating member 51 or 52 in meshing relationship with the sheet of flexible material 12a between the meshed portions of the ridges 53. The corrugating members 51 and 52 are mounted in axially parallel relationship to mesh portions of the ridges 53 of the corrugating members 51 and 52. While neither corrugating member 51 or 52 need be rotated (i.e., the sheet of flexible material 12c could be pulled between fixed guides shaped like the adjacent and other portions of the corrugating members that are contacted by the sheet of flexible material 12c at any one time), preferably at least the corrugating member 51 is rotated; and the sheet of flexible material 12c is fed between the meshed portions of the ridges 53 of the corrugating members 51 and 52 to generally conform the sheet of flexible material 12c to the periphery of the first corrugating member 51 and form the arcuate portions 13c of the sheet of flexible material 12c in the spaces between the ridges 53 of the first corrugating member 51 and the generally parallel anchor portions 14c of the sheet of flexible material 12c along the outer surfaces of the ridges 53. The formed sheet of flexible material 12c is retained along the periphery of the first corrugating member 51 after separation of the ridges 53; the spaced strands 16c of extruded molten elastic thermoplastic material from the die 22 are deposited along the formed sheet of flexible material 12c along the periphery of the first corrugating member 51 while the die is reciprocated axially of the corrugating members 51 and 52 so that the strands 16c form an undulating or generally sinusoidal or similar pattern with the strands bridging or extending between a plurality of the anchor portions 14c (i.e., at least two and, as illustrated, three anchor portions 14c), so that the molten strands partially envelope and adhere to the arcuate anchor portions 14c of the sheet of flexible material 12c at spaced anchor locations, after which the elastic sheet-like composite 50 is separated from the first corrugating member 51 and carried partially around the cooling roll 25 to complete cooling and solidification of its strands 16c.

The elastic sheet-like composite 50 made by the method illustrated in FIGS. 10 and 11 differs from the elastic sheet-like composite 10 made by the method illustrated in FIG. 1 in that the rows of bonding locations 18c and the rows of arcuate portions 13c of the sheet of flexible material 12c projecting from the strands 16c extend longitudinally in what is called the machine direction along the elastic sheet-like composite 50 instead of in what is called the cross direction or transversely across the elastic sheet-like composite as do the arcuate portions 13 in the elastic sheet-like composite 10. Also, while the plurality of generally parallel elongate extruded strands 16c of resiliently elastic thermoplastic material extend in generally parallel spaced relationship with each of the strands 16c having opposite elongate side surface portions that are spaced from and are adjacent the elongate side surface portions of adjacent strands 16c, the strands 16c extend in a parallel undulating, generally sinusoidal pattern with the strands bridging or extending between a plurality of the anchor portions 14c, rather than in a generally straight lines as do the strands 16 in the elastic sheet-like composite 10.

Figure 12:
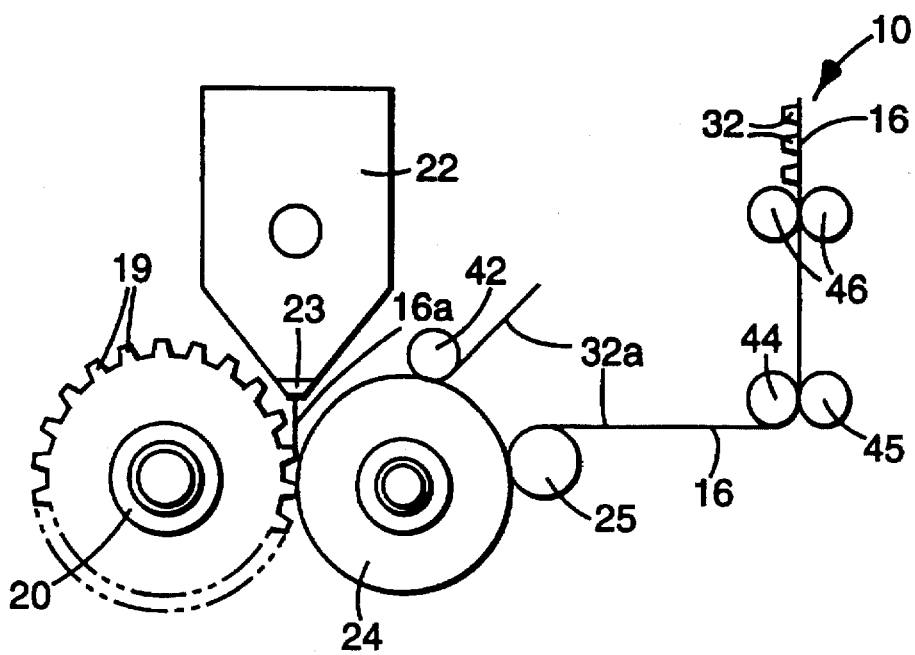
FIG. 12 is a schematic view illustrating a fifth embodiment of a method and equipment according to the present invention for making the first embodiment of the elastic sheet-like composite according to the present invention illustrated in FIGS. 2 and 3.

FIG. 12 illustrates a fifth embodiment of a method and equipment according to the present invention for making the elastic sheet-like composite 10 according to the present invention. The method illustrated in FIG. 12 is quite similar to and uses most of the same equipment as, the method illustrated in FIG. 9; and similar portions of that equipment have been given the same reference numerals and perform the same functions as they do in the equipment illustrated in FIG. 9. As a modification of the general method steps described above with reference to FIG. 9, the method illustrated in FIG. 12 does not use either the first sheet 12 of flexible material or the first corrugating member 21. The second sheet 32a of stretchable flexible material that when stretched will retain most of the shape to which it is stretched has one surface placed in closely spaced opposition to the ridges 19 on the ridged corrugating member 20 so that the extruder die 22 extrudes the spaced generally parallel elongate strands of molten thermoplastic material therebetween which are pressed by the ridges 19 onto the adjacent surface of the second sheet 32a of flexible material to form resiliently elastic strands 16 bonded to and extending between spaced locations along the surface of the second sheet 32a of flexible material; and then stretching the sheet-like composite 32a longitudinally of the strands 16 after they are cooled and solidified to permanently stretch the second sheet 32a of flexible material so that upon elastic recovery of the strands 16, the second sheet 32a of flexible material will have arcuate portions 33 projecting from corresponding side surface portions 28 of the strands 16. The equipment illustrated in FIG. 12 includes the second corrugating member 21, the extruder 22 and extruder die 23, the cooling and nipping rollers 24 and 25 which are operated in the manner described above with reference to FIG. 1; the nipping roller 42, the pair of nipping rollers 44 and 45 (the roller 44 may or may not be heated depending on the type of second sheet 32a being processed as noted above), and the pair of nipping rollers 46, all of which are operated in the manner described above with reference to FIG. 9, so that after the elastic sheet-like composite 10 moves past the nipping rollers 46 the strands 16 will return to their normal or un-stretched length, and the second sheet 32a of flexible material will have arcuate portions 33 projecting from corresponding side surface portions 28 of the strands 16.

Figure 13:
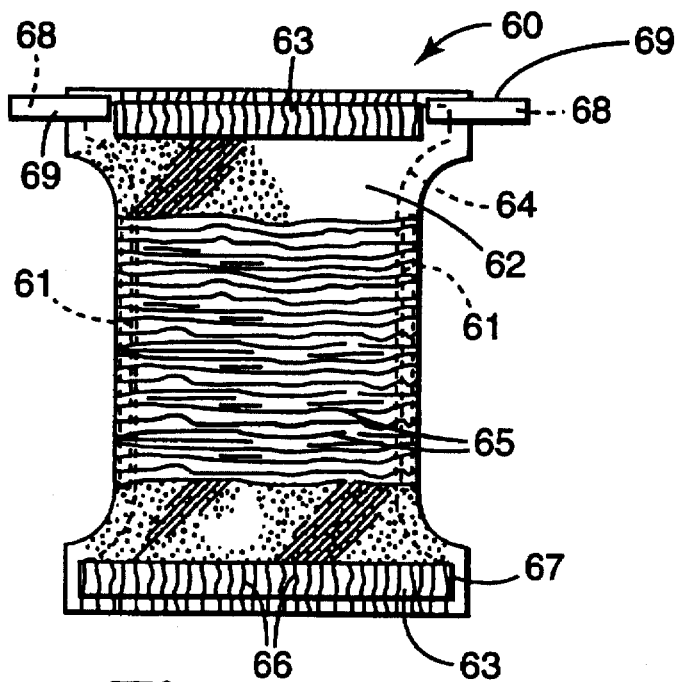
FIG. 13 is a plan view of a first embodiment of a disposable garment or diaper incorporating elastic sheet-like composite according to the present invention.

FIG. 13 illustrates a disposable garment or diaper 60 including a conventional flexible covering layer 62, and a layer 64 of conventional moisture absorbent padding 64 adhered to an inner surface of the covering layer 62. Two elongate strips 61 of the elastic sheet-like composite 10 illustrated in FIGS. 1, 2, and 3 in which the strands 16 extend longitudinally of the strips 61 are adhered along the inner surface of the covering layer 62 along the edges that will form the leg openings of the diaper 60 when it is used. Also, two strips 63 of the elastic sheet-like composite 30 illustrated in FIGS. 5 and 6 in which the strands 16 extend longitudinally of the strips 63 are adhered along the outer surface of the covering layer 62 along the edges that will form the waist opening of the diaper 60 when it is used. The outer surfaces of the first sheets 12 of flexible material on the two strips 61 of the elastic sheet-like composite 10 are adhered (while the strands 16 are under tension to flatten the two strips 61) surface to surface with the inner surface of the flexible covering layer 62 along the edges of the covering layer 62 that define the leg openings for the diaper 60 when the diaper 60 is in use so that the strands 16 cause the flexible covering layer 62 to have arcuate portions 65 projecting away from the elastic strands 16 corresponding to the arcuate portions 13 of the two strips 61 of the first sheet 12 of flexible material. Similarly, the outer surfaces of the first sheets 12 of flexible material of the two strips 63 of the elastic sheet-like composite 30 are adhered (while the strands 16 are under tension to flatten the strips 63) surface to surface with the outer surface of the flexible covering layer 62 along opposite edges thereof that define the waist opening of the diaper 60 when the diaper 60 is in use so that the strands 16 cause the flexible covering layer 62 to have arcuate portions 66 projecting away from the elastic strands 16 corresponding to the arcuate portions 13 of the first sheet 12 of flexible material. A sheet 67 of conventional loop material or nonwoven fibers or material that are bonded internally of the sheet either replaces the outer of the first or second sheets 12 or 32 of flexible material, or such a sheet 67 is adhered to the outer surface of the outer of the first or second sheet 12 or 32 of flexible material on the strip 63 of the elastic sheet-like composite 30 at one end of the diaper. That sheet 67 of loop or nonwoven material provides a loop fastener portion adapted to be engaged by hook fastener portions 68 of the type described in U.S. Pat. No. 4,894,060 (the content whereof is incorporated herein by reference) positioned or carried on the ends of tabs 69 at the other end of the diaper 60 to afford closing and opening of the diaper 60.

Among many alternative structures that could be provided for the disposable garment or diaper 60, the two strips 61 could be of the elastic sheet-like composites 30 or 50 illustrated in FIGS. 4, 5, and 6 or 10 and 11 respectively and/or the two strips 63 could be of the elastic sheet-like composites 10 or 50 illustrated in FIGS. 1, 2, and 3 or 10 and 11 respectively. The two strips 63 could be adhered to the inner surface of the of the flexible covering layer 62, and the tabs 68 could be replaced by lengths of pressure sensitive adhesive coated tape adapted to adhere to the outer surface of the flexible covering layer 62.

Figure 14:
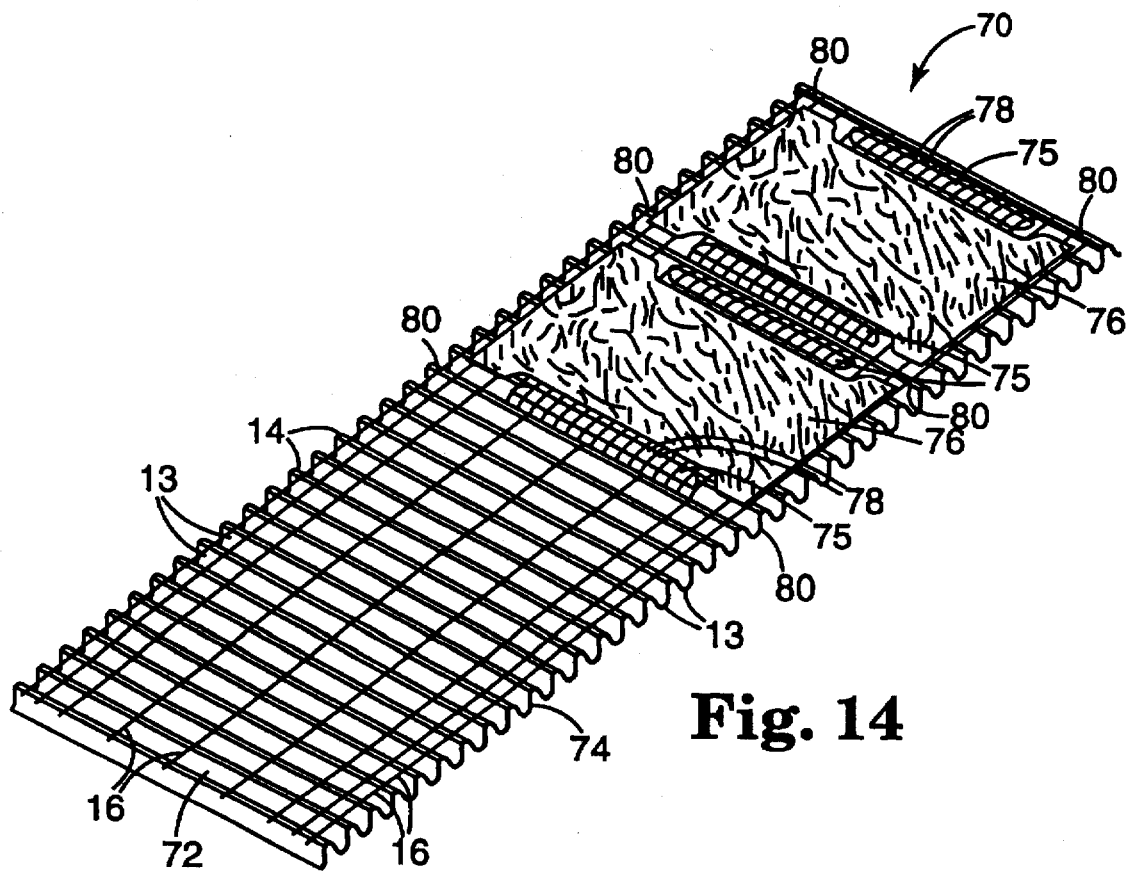
FIG. 14 is a perspective view of an assembly from which can be made a second embodiment of a disposable garment (i.e., a diaper or training pants) incorporating elastic sheet-like composite according to the present invention.

FIG. 14 illustrates an assembly 70 from which can be made disposable garments either in the form of diapers, training pants, or adult incontinence briefs. The assembly 70 was made using (1) a continuous length 72 of the elastic sheet-like composite 10 illustrated in FIGS. 2 and 3 modified (as was described with reference to FIG. 8) so that the strands 16 are more closely spaced and/or are optionally larger in diameter adjacent opposite edges 74 of the length 72 (alternatively the length 72 could be of the elastic sheet-like composite 30), and (2) a plurality of elongate strips 75 extending transversely to the length 72, which strips 75 are of the elastic sheet-like composite 10 illustrated in FIGS. 2 and 3 in which the strands 16 extend longitudinally of the strips 75 (alteratively the strips 75 could be made of the elastic sheet-like composite 50 or of other conventional elastic material used in this type of product). The first sheet 12 of flexible material included in the continuous length 72 of the elastic sheet-like composite 10 could be of a non elastic or of an elastic polymeric sheet material. Pre-cut pieces of conventional moisture absorbent padding 76 extending transverse of the continuous length 72 between its edges 74 are adhered in spaced relationship to the continuous length 72 over its side on which its strands 16 extend. The outer surfaces of the first sheets 12 of flexible material on the strips 75 are adhered to the continuous length 72 over its side on which its strands 16 extend. That adhesion is done while the strands 16 of both the strips 75 and the length 72 are under tension to flatten the two strips 75 and the length 72. The strips 75 are thus adhered along the opposite sides of each of the spaced pieces of padding 76 that are extending transverse of the length 72 and along which will be formed the leg openings for the diapers or training pants to be made incorporating the pieces of padding 76. The strands 16 of the strips 75 cause the length 72 to have arcuate portions 78 along the strips 75 that project away from those elastic strands 16 and are oriented at right angles to the arcuate portions 13 in the length 72 that are caused by its strands 16. Individual diapers may then be cut from the assembly 70 by cutting the length 72 transversely between the adjacent pieces of padding 76 and between adjacent strips 75 therebetween and adding to the side of length 72 opposite the pieces of padding 76 two projecting tabs and a sheet of nonwoven fibers that are bonded internally of the sheet or other loop material similar to and located as the tabs 69 and the sheet of nonwoven fibers or loop material 67 illustrated in FIG. 12. Alternatively if training pants are to be formed, the length 72 and pieces of padding 76 can be folded longitudinally of the length 72 to bring its edges 74 together with the folded padding 76 enclosed by the folded length 72, and portions 80 of the length 72 that will then be adjacent each other on opposite sides of the folded pieces of padding 76 can be attached together adjacent and for a short distance normal to the edges 74 by various means such as adhesives, chemical bonding, heat sealing, sonic welding, etc. The folded length 72 can be cut apart through the sealed portions 80 midway between the adjacent pieces of padding 76 and between the adjacent strips 75 therebetween to form individual training pants, each incorporating one of the pieces of padding 76 and two of the strips 75 around its leg openings.

Figure 15:
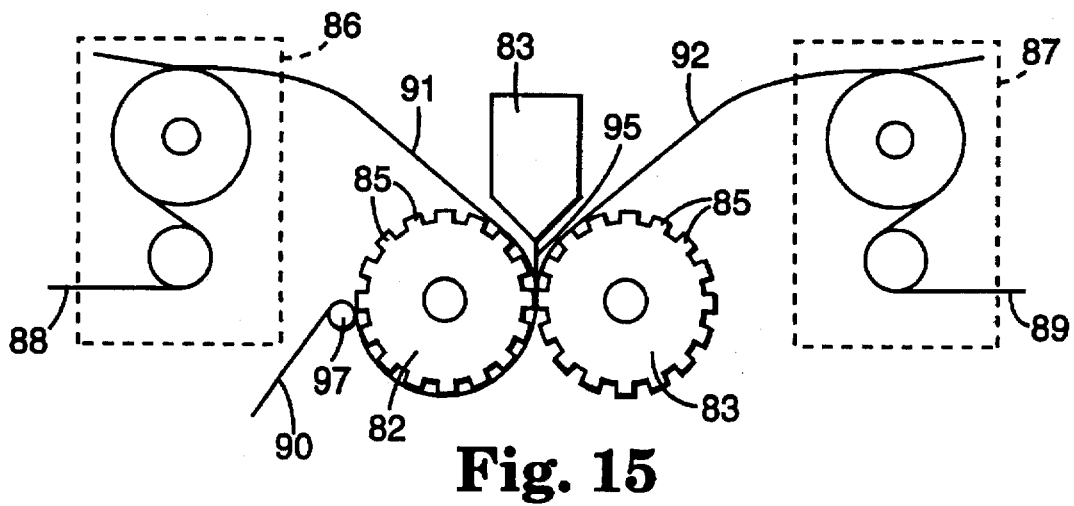
FIG. 15 is a schematic view illustrating a sixth embodiment of a method and equipment according to the present invention for making a fourth embodiment of the elastic sheet-like composite according to the present invention.
Figure 16:
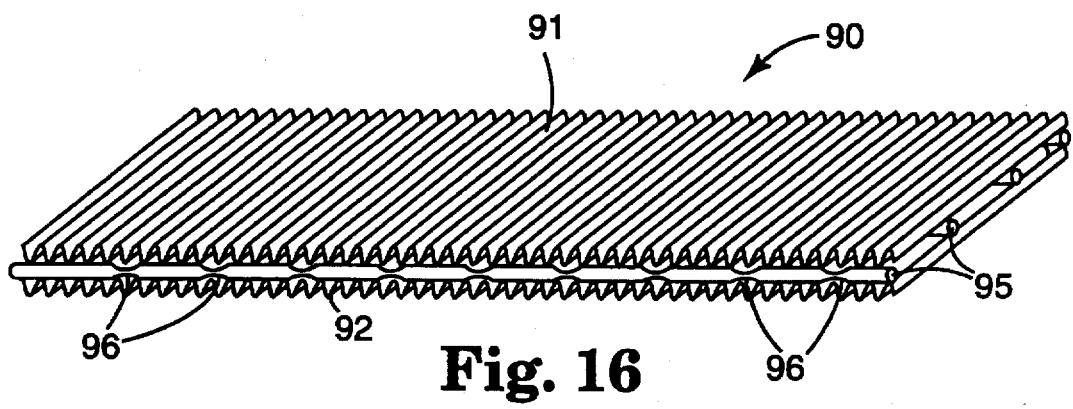
FIG. 16 is a perspective view of the fourth embodiment of the elastic sheet-like composite according to the present invention made by the method and equipment illustrated in FIG. 15.
Figure 17:
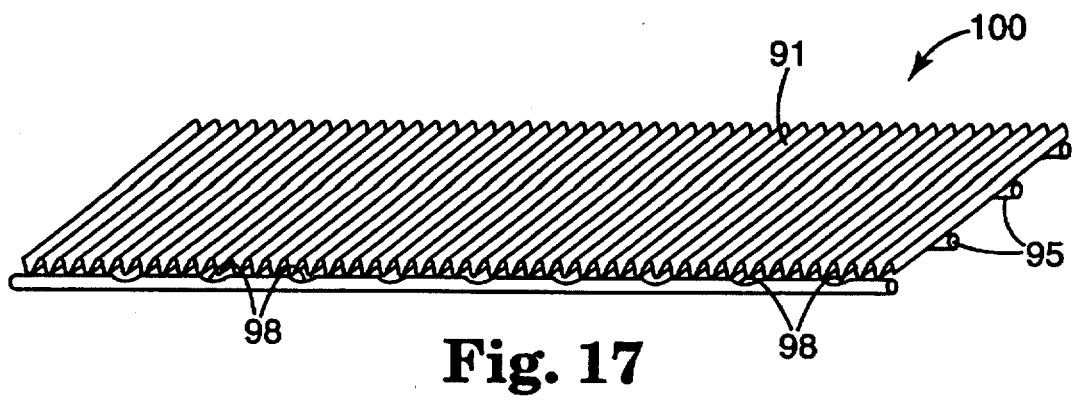
FIG. 17 is a perspective view of a fifth embodiment of the elastic sheet-like composite according to the present invention that can be made by the method and equipment illustrated in FIG. 15.

FIG. 15 illustrates a sixth embodiment of a method and equipment according to the present invention that can be used for making the fourth and fifth embodiments of elastic sheet-like composite 90 and 100 according to the present invention respectively illustrated in FIGS. 16 and 17.

The equipment illustrated in FIG. 15 includes first and second generally cylindrical bonding rollers 82 and 83 each having an axis and a periphery around that axis defined by circumferentially spaced ridges 85 generally parallel to the axes of the bonding rollers 82 and 83; means such as a frame for the equipment (not shown) for mounting the bonding rollers 82 and 83 in axially parallel relationship with the peripheries of the bonding rollers 82 and 83 defining a nip therebetween; means provided by a pair of sheet compacting devices 86 and 87 (e.g., the devices commercially designated "Micrex/Microcreper" equipment available from the Micrex Corporation, Walpole, Mass., which crinkles and compresses the fibers or materials of a sheet to form a sheet that is compacted in a first direction along its surfaces and can be easily expanded in that first direction by partial straightening of the fibers in the sheet) each adapted for receiving a sheet 88 or 89 of flexible material having opposite major surfaces; compacting that sheet 88 or 89 in a first direction parallel to its major surfaces (i.e., along its direction of travel through the device 86 or 87) so that the first and second compacted sheets 91 and 92 have opposite surfaces and can be extended in the first direction along those surfaces in the range of 1.1 to over 4 times its compacted length in the first direction; means for feeding the first and second compacted sheets 91 and 92 of flexible material into the nip in opposed relationship along the surfaces of the first and second bonding rollers 82 and 83; and means in the form of an extruder 83 that is essentially the same as the extruder 22 described above for extruding resiliently elastic thermoplastic material to form a multiplicity of generally parallel elongate molten strands 95 of the resiliently elastic thermoplastic material extending in generally parallel spaced relationship and for positioning the molten strands 95 between the opposed surfaces of the first and second compacted sheets 91 and 92 of flexible material in the nip between the first and second bonding rollers 82 and 83 with the stands 95 extending in the first direction along the first and second compacted sheets 91 and 92 where the strands 95 are thermally bonded to the first and second compacted sheets 91 and 92 at spaced bonding locations 96 along the strands 95 because of bonding pressure applied by the ridges 85. The elastic sheet-like composite 90 is retained along the periphery of the bonding roller 82 by a guide roller 97, and the bonding roller 82 is cooled (e.g., to 100 degrees Fahrenheit) to help solidify the strands 95.

As with the other sheets of flexible material described above, the compacted sheets 91 and 92 can be formed from many materials including non-woven fibers, or from polymeric film, and when the compacted sheets 91 and 92 and the strands 95 comprise generally the same thermoplastic material, the extruding strands 95 are fused to the compacted sheets 91 and 92 of flexible material.

The elastic sheet-like composite 90 made by the mechanism illustrated in FIG. 15 is illustrated in FIG. 16. That sheet-like composite 90 comprises in its un-stretched state (1) a multiplicity of the generally parallel elongate extruded strands 95 of resiliently elastic thermoplastic material extending in generally parallel spaced relationship, each of the strands 95 having opposite elongate side surface portions that are spaced from and are adjacent the elongate side surface portions of adjacent strands 95, and each of the strands 95 also having corresponding opposite first and second elongate surface portions extending between the opposite elongate side surface portions; and (2) the first and second compacted sheets 91 and 92 of flexible material having opposite major surfaces, and being compacted in a first direction along those first surfaces so that the first and second compacted sheets 91 and 92 can be extended in the first direction in the range of 1.1 to over 4 times its compacted length (and preferably over 1.3 times its compacted length) in the first direction. Those first and second compacted 91 and 92 are respectively thermally bonded to the first and second elongate surface portions of the strands 95 at the spaced bonding locations 96 with the strands 95 extending in the first direction to afford elastic extension of the strands 95 and the compacted sheets 91 and 92 in the first direction.

The equipment illustrated in FIG. 15 can be operated with only one of the sheets 88 or 89 of flexible material, in which case it will make an elastic sheet-like composite like the elastic sheet-like composite 100 illustrated in FIG. 17. That elastic sheet-like composite 100 comprises in its unstretched state (1) a multiplicity of the generally parallel elongate extruded strands 95 of resiliently elastic thermoplastic material extending in generally parallel spaced relationship, and only one compacted sheet 91 or 92 (identified as sheet 91 in the drawing) of flexible material that is compacted in a first direction along its surfaces so that the compacted sheet 91 or 92 can be extended in the first direction in the range of 1.1 to over 4 times its compacted length in the first direction. The compacted sheet 91 or 92 is thermally bonded to the first elongate surface portions of the strands at spaced bonding locations 98 with the strands extending in the first direction to afford elastic extension of the strands and the compacted sheet 91 in the first direction.

Figure 18:
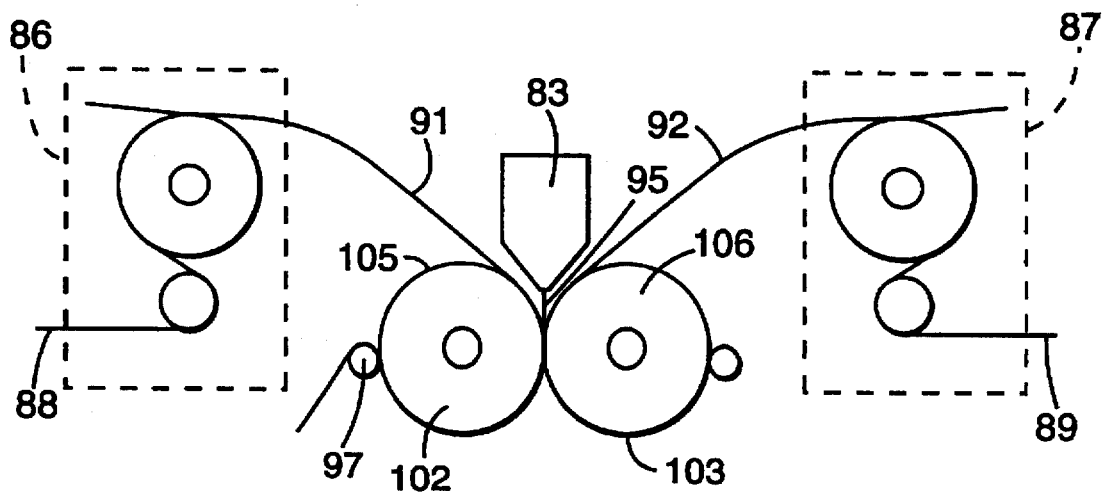
FIG. 18 is a schematic view illustrating a sixth embodiment of a method and equipment according to the present invention for making sixth and seventh embodiments of the elastic sheet-like composite according to the present invention.

FIG. 18 illustrates a sixth embodiment of a method and equipment according to the present invention that can be used for making embodiments of elastic sheet-like composite that are very similar to the embodiments of elastic sheet-like composites 90 and 100 respectively illustrated in FIGS. 16 and 17, except that the strands 95 are thermally bonded to the compacted sheets 91 and/or 92 along essentially the entire lengths of the strands 95 rather than having longitudinally spaced parts of the strands thermally bonded to the first compacted sheets at spaced bonding locations 96 or 98 along the strands 95.

Parts of the equipment illustrated in FIG. 18 that are the same as parts of the equipment illustrated in FIG. 15 have been given the same reference numerals and provide the same function. The equipment illustrated in FIG. 18 differs only from the equipment illustrated in FIG. 15 in that first and second generally cylindrical bonding rollers 102 and 103 used in that equipment have peripheries 105 and 106 respectively around their axis that are cylindrical so that the strands 95 are thermally bonded to the first and second compacted sheets 91 and 92 along their entire lengths.

EXAMPLES

Example 1

Elastic sheet-like composite similar to the elastic sheet-like composite 10 illustrated in FIG. 2 was made using equipment similar to that illustrated in FIG. 1 using the following mixture in the extruder 22 to form the strands 16; ninety percent (90%) of a thermoplastic synthetic rubber commercially designated Kraton 1657 that is commercially available from Shell Chemical Co., Houston, Tex.; two percent (2%) of a coloring agent commercially designated CBE 101P White commercially available from Spectrum Colors, Minneapolis, Minn.; three percent (3%) of a slip agent commercially designated Ampacet 10110 and available from Ampacet Corp., Mount Vernon, N.Y.; and five percent (5%) of an anti blocking material commercially designated CBE 13782E that is available from Spectrum Colors. About ten strands 16 per inch of that material having diameters of about 0.05 centimeter or 0.020 inch were applied by equipment similar to that illustrated in FIG. 1 to corrugated first sheets 12 of different materials including (1) 3M brand porous film (XMO-8-044), (2) 0.0036 centimeter or 0.0014 inch thick polyethylene of the type commonly used in diapers, and (3) nonwoven material comprising polypropylene staple fibers thermally point bonded together. All of the elastic sheet-like composites described above in this paragraph had good elastic properties and did not neck down when extended within the limit of straightening the first sheets 12.

Example 2

Elastic sheet-like composite similar to the elastic sheet-like composite 30 illustrated in FIG. 5 was made using the same mixture in the extruder 22 described in the preceding paragraph to form the strands 16a. About ten strands 16 per inch of that material having diameters of about 0.05 centimeter or 0.020 inch were applied by equipment similar to that illustrated in FIG. 9 to a corrugated first sheet 12 of nonwoven flexible material comprising polypropylene staple fibers thermally point bonded together, and a non-corrugated second sheet 32a of 3M brand porous film (XMO-8-044), which is a stretchable porous polymeric film material that when stretched will retain most of the shape to which it is stretched, to form the structure extending from the periphery of the roll 24 to the rollers 44 and 45 in FIG. 9. The two sets of rollers 44, 45 and 46 were not used; rather that structure was manually stretched to provide the function of the rollers 44, 45 and 46. The resulting elastic sheet-like composite 30 had arcuate portions 33 of the sheet 32a projecting from corresponding side surface portions 28 of the strands 16 on the side of the strands 16 opposite the sheet 12 of nonwoven flexible material, thus providing the elastic strands 16 between the corrugated nonwoven sheet 12 and the corrugated porous film sheet 32a. The resulting sheet material 30 had good elastic properties and did not neck down when extended within the limit of straightening the first and second sheets 12 and 32a.

Example 3

Elastic sheet-like composite similar to the elastic sheet-like composite 10 illustrated in FIG. 2 was made using equipment similar to that illustrated in FIG. 1. A thermoplastic rubber commercially available under the trade name "Kraton G1657X" from Shell Chemical Company, A Division of Shell Oil Company, Atlanta, Ga., was placed in the extruder 22 to form the strands 16. About ten strands 16 per inch of that material at a basis weight of 20 grams per square meter were applied by the equipment to a corrugated first sheet 12 of loop material formed of 0.8 ounces per square yard spunbond polypropylene commercially available under the trade name "Fiberweb Celestra" from FiberWeb North America, Inc., Simpsonville, S.C. That material was compacted approximately 30% using the Micrex process described above which softened the material and placed a micro structured loop pattern in the cross direction of the nonwoven material that allowed for longitudinal stretching of the material and engagement of hooks so that the material provided the loop portion of a hook and loop fastener. The first sheet 12 was corrugated in the cross direction between the corrugation rollers 20 and 21 to form 7 corrugations per inch, then bonded to the strands 16 by the ridges 19 in a nip between the corrugation roll 20 and the smooth chill roll 24. The corrugation roll 21 was at about 190 F; the corrugation roll 20 was at about 230 F, and the chill roll 24 was at about 85 F. The line speed was about 15 feet per minute, and the melt temperature in the extruder 22 was about 430 F. The sheet of loop material 10 produced was soft, breathable and inexpensive, had arcuate portions 33 projecting from the strands 16 that were 0.012 inch in height and width, was stretchable in the machine direction and had good elastic properties, and did not neck down when extended to straighten the first sheet 12 and to extend the length of the first sheet 12. The sheet of loop material 10 produced would have many uses, including as a side panel and/or as the loop portion of a hook and loop fastener.

Example 4

Elastic sheet-like composite similar to the elastic sheet-like composite 10 illustrated in FIG. 2 was made with the equipment illustrated in FIG. 12, except that the two pairs of nipping rollers 44, 45 and 46 were not used. A thermo-plastic rubber commercially available under the trade name "Kraton G1657X" from Shell Chemical Company, A Division of Shell Oil Company, Atlanta, Ga., was used in the extruder 22 to form the strands 16. No first sheet 12 was used. About ten strands 16 per inch of that material that provided a basis weight of 20 grams per square meter of the strand material were applied by the equipment to a second sheet 32a of loop material formed of hydro-entangled Rayon/Polyester with a basis weight 56 grams per square meter commercially available under the trade name "Veratec VersaIon" from Veretec, A Division of International Paper, Walpole, Mass. That material was compacted approximately 40% (i.e., the compacted material could then be extended to 2.5 times its compacted length) using the Micrex process described above which softened the material and placed a micro structured loop pattern in the cross direction of the nonwoven material that allowed for longitudinal stretching of the material and engagement of hooks so that the material provided the loop portion of a hook and loop fastener. The second sheet 32a was bonded at spaced locations to the strands 16 in the nip between the corrugation roll 20 and the smooth chill roll 24 by the ridges 19 of the corrugation member or roll 20. The corrugation roll 20 was at about 230 F, and the chill roll was at about 85 F. The line speed was about 15 feet per minute, and the melt temperature in the extruder 22 was about 425 F. The sheet of loop material produced was initially flat with the entire second sheet 32a lying against the strands 16, but was manually stretch in the machine direction and released so that the strands 16 returned to their original lengths and the portions of the second sheet 32a between the portions thereof attached to the strands 16 formed arcuate portions 13 about 0.012 inch wide at the strands 16 and approximately 0.06 inch in height from the strands 16. Before such stretching, the loop material produced could be wound flat on a roll which produced a roll that was more dense and thus more easily shipped and stored than a roll of the same material after it was stretched and released. The elastic sheet-like composite 10 thus produced was soft, breathable and inexpensive, had good elastic properties, did not neck down when extended to straighten the first sheet 12 and/or to extend the length of the first sheet 12, and was deemed useful as a side panel on a child or adult incontinent diaper or on a training pant, or as the loop portion of a hook and loop fastener, or as an elastic wrap.

Example 5

An elastic sheet-like composite similar to the elastic sheet-like composite 30 illustrated in FIG. 5 was made using the equipment illustrated in FIG. 4. A thermoplastic rubber commercially available under the trade name "Kraton G1657X" from Shell Chemical Company, A Division of Shell Oil Company, Atlanta, Ga., was used in the extruder 22 to form the strands 16. About ten strands 16 per inch of that material that had a basis weight of about 40 grams per square meter were extruded at a temperature of 450 degree F between two sheets 12 and 32 of spunbonded non-woven point bonded material that had a basis weight of 0.5 ounce per square yard and were commercially available under the trade name "Amoco RFX", identification 9.585A, from Amoco Fabric and Fibers Company, Atlanta Ga. The sheets 12 and 32 of material were corrugated by the pairs of mating corrugating members or rollers 20, 21 and 36, 37 respectively, which pairs of corrugating members were identical and were synchronized to move the ridges 19 and 38 of the corrugating members 20 and 24 in opposed relationship through the nip between the rollers 20 and 36 as is illustrated in FIG. 4, and to thereby place the anchor portions 14 and 34 of the sheets 12 and 32 of material opposite each other on the strands 16 as is illustrated in FIG. 5. The surface speed of the corrugating members 20 and 36 was 20 feet per minute. The corrugating members 36 and 20 were heated to 230 degree F and had rough textured surface finishes to assist in holding the sheets 12 and 32 of material along their surfaces between the corrugating members 21 and 37 and the nip between the corrugating members 36 and 20 at which the strands were adhered between the anchor portions 14 and 34 of the sheets 12 and 32 of material. The corrugating members 21 and 37 were heated to 200 degree F and had a very smooth polished chrome surfaces to facilitate their release from the sheets 12 and 32 of material along the corrugating members 21 and 37. The resultant sheet of elastic material had arcuate portions 13 and 33 that projected from the strands 16 by about 2.5 millimeters, had an overall thickness un-stretched of about 5 millimeters, could be stretched longitudinally of the strands 16 to about 1.8 times its un-stretched length, and did not neck down sideways when it was thus stretched. The resultant sheet of elastic material was very soft and conformable, and was deemed suitable for many uses, including as a side panel on a diaper, as the loop portion of a hook and loop fastener or as a medical wrap.

Example 6

An elastic sheet-like composite similar to the elastic sheet-like composite 90 illustrated in FIG. 16 was made with the equipment illustrated in FIG. 15 except that the bonding roller 83 had a smooth cylindrical periphery. The two sheets 88 and 89 of material used were the spunbonded point bonded nonwoven material having a basis weight of 0.5 oz/square yard that is sold under the trade name "Amoco RFX", identification 9.585A by Amoco Fabric and Fibers Company, Atlanta Ga. The two sheets 88 and 89 were compacted to 30% of their original length (3:1 compaction) by the Micrex process described above using the sheet compacting devices 86 and 87. The compacted sheets 91 and 92 were directed along the peripheries of the bonding rollers 82 and 83 on opposite sides of the curtain of molten strands 95 as is illustrated in FIG. 15. A thermoplastic rubber commercially available under the trade name "Kraton G1657X" from Shell Chemical Company, A Division of Shell Oil Company, Atlanta Ga., was used in the extruder 83 to form the strands 95. About ten strands 95 per inch of that material that had a basis weight of about 40 grams per square meter were extruded at a temperature of 450 degrees Fahrenheit between the two compacted sheets 91 and 92 along the peripheries of the bonding rollers 82 and 83. The bonding rollers 82 and 83 point bonded the strands 95 to the compacted sheets 91 and 92 at about 7 bonding location 96 per inch, although additional bonding between these bonding location 96 were noted. The resultant elastic sheet-like composite 90 was soft, exhibited good elastic properties and did not neck down when elongated to the maximum non compacted lengths of the first and second sheets 88 and 89. The elastic sheet-like composite 90 appeared to have many potential uses, such as a loop portion of a hook and loop fastener, a diaper side panel, a medical bandage or as a headband.

Example #7

An elastic sheet-like composite similar to the elastic sheet-like composite 100 illustrated in FIG. 17 was made with the equipment illustrated in FIG. 15 and described in example 6 except that only one sheet 88 of the sheet material described in Example 6 that was compacted about 3:1 to form the compacted sheet 91 was used to form the elastic sheet-like composite. The resulting elastic sheet-like composite was soft, conformable and did not neck down once stretched. The exposed side of the elastic strands 95 exhibited good cohesion to the elastic sheet-like composite when it was wrapped on itself. Apparent potential uses included a low cost medical wrap or as a side panel on a diaper.

Example 8

An elastic sheet-like composite similar to the elastic sheet-like composite 90 illustrated in FIG. 16 (except that it did not have the specific bonding locations 96) was made with the equipment illustrated in FIG. 18 in which the bonding rollers 102 and 103 both have smooth cylindrical peripheries 105 and 106. The two sheets 88 and 89 of material used were the spunbonded material sold under the trade designation "Celestra 0.5 oz PP spunbond" by FiberWeb North America, Inc., Simpsonville, S.C. The two sheets 88 and 89 were compacted to 50% of their original length (2:1 compaction) by the Micrex process described above using the sheet compacting devices 86 and 87. The compacted sheets 91 and 92 were directed along the peripheries of the bonding rollers 102 and 103 on opposite sides of the curtain of molten strands 95 as is illustrated in FIG. 18. A thermoplastic rubber commercially available under the trade name "Kraton G1657X" from Shell Chemical Company, A Division of Shell Oil Company, Atlanta Ga., was used in the extruder 83 to form the strands 95. About ten strands 95 per inch of that material that had a basis weight of about 35 grams per square meter were extruded at a temperature of 450 degrees Fahrenheit between the two compacted sheets 91 and 92 along the peripheries of the bonding rollers 82 and 83. The bonding rollers 102 and 103 bonded the strands 95 to the compacted sheets along their entire lengths. The resultant elastic sheet-like composite was soft, exhibited good elastic properties and did not neck down when elongated to the maximum non compacted lengths of the first and second sheets 88 and 89.

The present invention has now been described with reference to several embodiments and modifications thereof. It will be apparent to those skilled in the art that many changes can be made in the embodiments described without departing from the scope of the present invention. Thus the scope of the present invention should not be limited to the structures and methods described in this application, but only by structures and methods described by the language of the claims and the equivalents of those structures and methods.

We claim:

1. An elastic sheet-like composite comprising:

a multiplicity of generally parallel elongate extruded strands of resiliently elastic thermoplastic material extending in generally parallel spaced relationship, each of said strands having opposite elongate side surface portions that are spaced from and are adjacent the elongate side surface portions of adjacent strands, and each of said strands also having corresponding opposite first and second elongate surface portions extending between said opposite elongate side surface portions; and a first sheet of flexible material having opposite major surfaces, said flexible material having spaced anchor portions thermally bonded at first sheet bonding locations to longitudinally spaced parts of the strands along said first elongate surface portions, and having arcuate portions projecting from said elastic strands between said first sheet bonding locations;

the bonds between said strands and said anchor portions at said first sheet bonding locations extending along the entire parts of the side surface portions of the strands that are closely adjacent the anchor portions, and the strands having uniform morphology along their lengths including at said bonding locations;

said first sheet being formed of nonwoven fibers that are bonded internally of the sheet, said fibers being crinkled and compressed within the first sheet so that the first sheet can be easily expanded by partial straightening of the fibers in the first sheet and can allow the elastic sheet-like composite to be expanded past the condition where the major surfaces of the first sheet is straightened.

2. An elastic sheet-like composite comprising:

a multiplicity of generally parallel elongate extruded strands of resiliently elastic thermoplastic material extending in generally parallel spaced relationship, each of said strands having opposite elongate side surface portions that are spaced from and are adjacent the elongate side surface portions of adjacent strands, and each of said strands also having corresponding opposite first and second elongate surface portions extending between said opposite elongate side surface portions; and a sheet of nonwoven fibers having opposite major surfaces, said fibers being bonded internally of the sheet and crinkled and compressed within the sheet so that the sheet can be easily stretched in a first direction by partial straightening of the fibers in the sheet and when stretched in said first direction will retain most of the length to which it is stretched, said sheet having spaced anchor portions thermally bonded to longitudinally spaced parts of the strands along said first elongate surface portions at bonding locations;

the elastic sheet-like composite being stretchable past the condition where the major surfaces of the sheet are straightened, such stretching and release of the sheet-like composite causing arcuate portions of the sheet to project from said elastic strands between said first sheet bonding locations.

3. An elastic sheet-like composite comprising:

a multiplicity of generally parallel elongate extruded strands of resiliently elastic thermoplastic material extending in generally parallel spaced relationship, each of said strands having opposite elongate side surface portions that are spaced from and are adjacent the elongate side surface portions of adjacent strands, and each of said strands also having corresponding opposite first and second elongate surface portions extending between said opposite elongate side surface portions;

a first sheet of flexible material having opposite major surfaces, said first sheet having spaced anchor portions thermally bonded at first sheet bonding locations to longitudinally spaced parts of the strands along said first elongate surface portions, and having arcuate portions projecting from said elastic strands between said first sheet bonding locations; and a second sheet of flexible material having opposite major surfaces, said second sheet having anchor portions thermally bonded at second sheet bonding locations to longitudinally spaced parts of the strands along said second elongate surface portions, and having arcuate portions projecting from said second elongate surface portions of the elastic strands between said second sheet bonding locations;

the bonds between said strands and said anchor portions at said first sheet bonding locations extending along the entire parts of the side surface portions of the strands that are closely adjacent the anchor portions, and the strands having uniform morphology along their lengths including at said bonding locations;

at least one of said first and second sheets being formed of nonwoven thermoplastic fibers that are bonded internally of the sheet, said fibers being crinkled and compressed within the sheet so that sheet can be easily expanded by partial straightening of the fibers in the sheet.

4. An elastic sheet-like composite according to claim 3 wherein both of said sheets are formed of nonwoven thermoplastic fibers that are bonded internally of the sheet, said fibers being crinkled and compressed within said sheets so that said sheets can be easily expanded by partial straightening of the fibers in the sheet and can allow the elastic sheet-like composite to be expanded past the condition where the major surfaces of the sheets of crinkled and compressed fibers are straightened.

5. An unstretched elastic sheet-like composite comprising:

a multiplicity of generally parallel elongate extruded strands of resiliently elastic thermoplastic material extending in generally parallel spaced relationship, each of said strands having opposite elongate side surface portions that are spaced from and are adjacent the elongate side surface portions of adjacent strands, and each of said strands also having corresponding opposite first and second elongate surface portions extending between said opposite elongate side surface portions; and an unstretched sheet of stretchable flexible material having opposite major surfaces, said sheet when stretched in a first direction, will retain most of the length to which it is stretched, said unstretched sheet having spaced anchor portions thermally bonded to longitudinally spaced parts of the strands along said first elongate surface portions at spaced bonding locations;

the elastic sheet-like composite being stretchable past the condition where the major surfaces of the unstretched sheet are straightened, such stretching and release of the sheet-like composite causing arcuate portions of the sheet to project from said elastic strands between said spaced bonding locations.

6. An elastic sheet-like composite according to claim 5 wherein said bonding locations are spaced about the same distances from each other and are aligned in generally parallel rows extending transverse of said strands to form continuous rows of said arcuate portions projecting about the same distance from said first surface portions of said strands when the elastic sheet-like composite is stretched and subsequently released.

7. An elastic sheet-like composite according to claim 5 wherein said bonding locations are in a regular pattern on said strands to form a corresponding pattern of said arcuate portions along said first surface portions of said strands when the elastic sheet-like composite is stretched and subsequently released.

8. An elastic sheet-like composite according to claim 5 wherein said elastic strands and said first sheet comprise the same thermoplastic material, and said strands are fused to said sheet at said bonding locations.

9. An elastic sheet-like composite comprising:

a multiplicity of generally parallel elongate extruded strands of resiliently elastic thermoplastic material extending in generally parallel spaced relationship, each of said strands having opposite elongate side surface portions that are spaced from and are adjacent the elongate side surface portions of adjacent strands and having a width between said opposite elongate side surface portions, and each of said strands also having corresponding opposite first and second elongate surface portions extending between said opposite elongate side surface portions; and a first sheet of flexible material having spaced anchor portions thermally bonded at first sheet bonding locations to longitudinally spaced parts of the strands along said first elongate surface portions, and having arcuate portions projecting from said elastic strands between said first sheet bonding locations;

the widths of said strands at said first sheet bonding locations are greater than the widths of said strands between said first sheet bonding locations and said strands at said first sheet bonding locations are formed around and indented by the arcuate convex surfaces of the anchor portions at said first sheet bonding locations so that the bonds between said strands and said anchor portions at said first sheet bonding locations extend along the entire parts of the side surface portions of the strands that are closely adjacent the anchor portions to provide firm attachment between said first sheet and said strands, and the strands have uniform morphology along their lengths including at said first sheet bonding locations.

10. An elastic sheet-like composite according to claim 9 wherein said first sheet is a thermoplastic film.

11. An elastic sheet-like composite according to claim 9 wherein said first sheet is formed of nonwoven fibers that are bonded internally of the sheet.

12. An elastic sheet-like composite according to claim 9 wherein said first sheet bonding locations are spaced about the same distances from each other and are aligned in generally parallel rows extending transverse of said strands to form continuous rows of said arcuate portions projecting about the same distance from said first surface portions of said strands.

13. An elastic sheet-like composite according to claim 9 wherein said first sheet bonding locations are in a regular pattern on said strands to form a corresponding pattern of said arcuate portions along said first surface portions of said strands.

14. An elastic sheet-like composite according to claim 9 wherein said elastic strands and said first sheet comprise the same thermoplastic material, and said strands are fused to said sheet at said first sheet bonding locations.

15. An elastic sheet-like composite according to claim 9 further including a second sheet of flexible material having anchor portions thermally bonded at second sheet bonding locations to longitudinally spaced parts of the strands along said second elongate surface portions, and having arcuate portions projecting from said second elongate surface portions of the elastic strands between said second sheet bonding locations.

16. An elastic sheet-like composite according to claim 15 wherein at least one of said first and second sheets is of thermoplastic film.

17. An elastic sheet-like composite according to claim 15 wherein said first sheet is a thermoplastic film and said second sheet is formed of thermoplastic fibers.

18. An elastic sheet-like composite according to claim 15 wherein at least one of said first and second sheets is formed of nonwoven thermoplastic fibers that are bonded internally of the sheet.

19. An elastic sheet-like composite comprising in its un-stretched state:

a multiplicity of generally parallel elongate extruded strands of resiliently elastic thermoplastic material extending in generally parallel spaced relationship, each of said strands having opposite elongate side surface portions that are spaced from and are adjacent the elongate side surface portions of adjacent strands, and each of said strands also having corresponding opposite first and second elongate surface portions extending between said opposite elongate side surface portions; and a first compacted sheet of flexible material having opposite major surfaces, said flexible material being compacted between said surfaces in a first direction along said surfaces by being crinkled and compressed in said first direction so that said first compacted sheet can be extended in said first direction in the range of 1.1 to over 4 times its compacted length in said first direction, said first compacted sheet being thermally bonded to said first elongate surface portions of said strands with said strands extending in said first direction to afford elastic extension of said strands and said first compacted sheet in said first direction.

20. An elastic sheet-like composite according to claim 19 wherein the strands are thermally bonded to said first compacted sheet along essentially the entire lengths of said strands.

21. An elastic sheet-like composite according to claim 19 wherein said first compacted sheet is a thermoplastic film.

22. An elastic sheet-like composite according to claim 19 wherein said first compacted sheet is formed of non-woven fibers that are bonded internally of the sheet.

23. An elastic sheet-like composite according to claim 19 wherein said elastic strands and said first compacted sheet comprise the same thermoplastic material, and said strands are fused to said sheet.

24. An elastic sheet-like composite according to claim 19 wherein said first compacted sheet is compacted between said surfaces in said first direction so that said first sheet can be extended in said first direction by at least 1.3 times its compacted length.

25. An elastic sheet-like composite according to claim 19 wherein longitudinally spaced parts of the strands are thermally bonded to said first compacted sheet at spaced bonding locations along said strands.

26. An elastic sheet-like composite according to claim 25 wherein said bonding locations are spaced about the same distances from each other and are aligned in generally parallel rows extending transverse of said strands to afford forming continuous rows of arcuate portions of said first compacted sheet projecting from said first surface portions of said strands when said sheet-like composite is elastically extended in said first direction and allowed to return to its un-stretched state.

27. An elastic sheet-like composite according to claim 19 further including a second compacted sheet of flexible material having opposite major surfaces, said second compacted sheet of flexible material being compacted between said surfaces in a first direction along said surfaces by being crinkled and compressed in said first direction so that said second compacted sheet can be extended in said first direction in the range of 1.1 to over 4 times its compacted length in said first direction, said second compacted sheet being thermally bonded to said second elongate surface portions of said strands with said strands extending in said first direction to afford elastic extension of said strands and both of said compacted sheets in said first direction.

28. An elastic sheet-like composite according to claim 27 wherein at least one of said first and second compacted sheets is of thermoplastic film.

29. An elastic sheet-like composite according to claim 27 wherein said first compacted sheet is a thermoplastic film and said second compacted sheet is formed of thermoplastic fibers.

30. An elastic sheet-like composite according to claim 27 wherein at least one of said first and second compacted sheets is formed of non-woven thermoplastic fibers that are bonded internally of the sheet.

* * * * *